United States Patent
Johnson

(10) Patent No.: US 10,285,802 B2
(45) Date of Patent: May 14, 2019

(54) DEVICES, SYSTEMS, AND METHODS FOR TRABECULAR MESHWORK EXTENSION

(71) Applicant: Novartis AG, Basel (CH)

(72) Inventor: Andrew David Johnson, Laguna Niguel, CA (US)

(73) Assignee: Novartis AG, Basel (CH)

( * ) Notice: Subject to any disclaimer, the term of this patent is extended or adjusted under 35 U.S.C. 154(b) by 274 days.

(21) Appl. No.: 15/237,944

(22) Filed: Aug. 16, 2016

(65) Prior Publication Data
US 2018/0049864 A1    Feb. 22, 2018

(51) Int. Cl.
*A61F 2/14*      (2006.01)
*A61M 39/00*   (2006.01)
*A61F 9/007*    (2006.01)

(52) U.S. Cl.
CPC ............... *A61F 2/142* (2013.01); *A61F 2/15* (2015.04); *A61F 9/00781* (2013.01); *A61F 2220/0016* (2013.01); *A61F 2250/0012* (2013.01)

(58) Field of Classification Search
CPC .... A61F 2/142; A61F 2/15; A61F 2250/0012; A61F 2220/0016; A61F 9/00781; A61F 2009/00868
See application file for complete search history.

(56) References Cited

U.S. PATENT DOCUMENTS

| | | | | |
|---|---|---|---|---|
| 6,217,594 B1* | 4/2001 | Hallen | ............... | A61B 17/0057 606/157 |
| 2004/0087886 A1* | 5/2004 | Gellman | ................... | A61F 2/88 604/8 |
| 2004/0181138 A1* | 9/2004 | Hindricks | .......... | A61B 18/1492 600/374 |
| 2004/0193262 A1* | 9/2004 | Shadduck | ........... | A61F 9/00781 623/4.1 |
| 2007/0082750 A1* | 4/2007 | Rose | ...................... | A63B 53/14 473/300 |
| 2007/0218269 A1* | 9/2007 | Kato | .......................... | C09J 7/22 428/304.4 |
| 2007/0221230 A1* | 9/2007 | Thompson | ....... | A61B 17/12022 128/207.15 |
| 2008/0154169 A1* | 6/2008 | Kase | ..................... | A61F 13/023 602/55 |
| 2009/0227934 A1 | 9/2009 | Euteneuer et al. | | |
| 2010/0160871 A1* | 6/2010 | Seegert | .................. | A61B 17/30 604/290 |
| 2011/0130821 A1* | 6/2011 | Styrc | ......................... | A61F 2/95 623/1.11 |
| 2011/0196487 A1* | 8/2011 | Badawi | ............... | A61F 9/00781 623/4.1 |

(Continued)

*Primary Examiner* — Adam Marcetich

(57) ABSTRACT

Described herein is an extension device to extend ocular tissue within an irideocorneal angle of an eye of a patient, comprising a flexible body and a plurality of tensioning features disposed on the body. The body is sized and configured to be disposed within the irideocorneal angle. The body has a curved longitudinal axis, a channel extending from a first end to a second end, an inner convex side, and an outer concave side. The body is flexible between a first flexed condition and a second unflexed condition. The body has a first radius of curvature in the first flexed condition and a second radius of curvature in the unflexed condition. Each tensioning feature is shaped and sized to grasp the ocular tissue within the irideocorneal angle.

20 Claims, 18 Drawing Sheets

(56) References Cited

U.S. PATENT DOCUMENTS

| | | | |
|---|---|---|---|
| 2012/0116415 A1* | 5/2012 | Forsell | A61B 17/29 606/119 |
| 2012/0220917 A1 | 8/2012 | Silvestrini et al. | |
| 2013/0035551 A1 | 2/2013 | Yu et al. | |
| 2013/0158462 A1* | 6/2013 | Wardle | A61F 9/00781 604/8 |
| 2014/0180225 A1* | 6/2014 | Dunn | A61M 1/0088 604/319 |
| 2015/0223976 A1 | 8/2015 | Bouch et al. | |

* cited by examiner

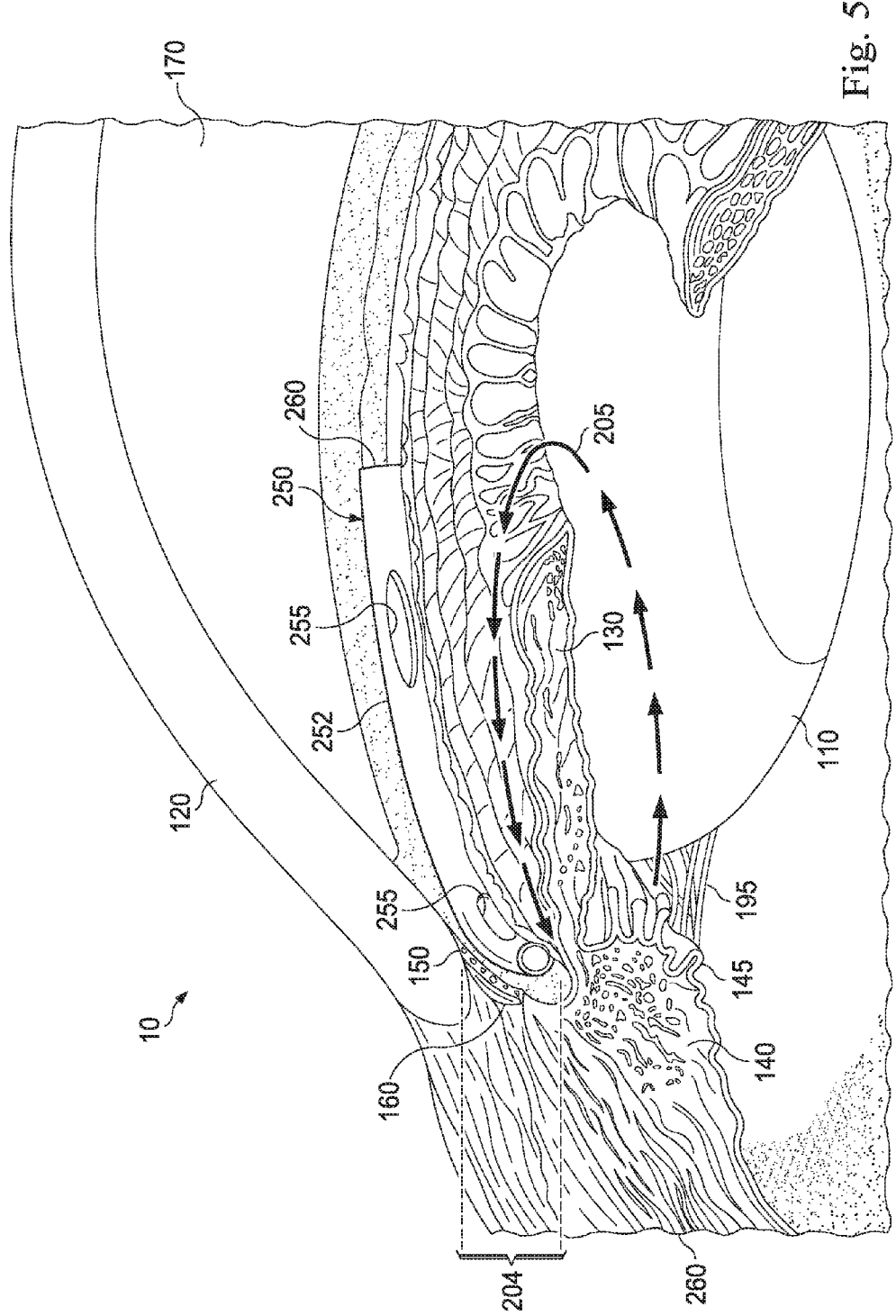

DEVICES, SYSTEMS, AND METHODS FOR TRABECULAR MESHWORK EXTENSION

BACKGROUND

The present disclosure relates generally to intraocular pressure/flow control systems and methods for treating a medical condition. In some instances, embodiments of the present disclosure are configured to be part of a system for the treatment of ophthalmic conditions.

Glaucoma, a group of eye diseases affecting the retina and optic nerve, is one of the leading causes of blindness worldwide. The tissue pressure of the intraocular contents is called the intraocular pressure (IOP). In general, vision loss from glaucoma results when the IOP increases to pressures above normal for prolonged periods of time. IOP can increase due to high resistance to the drainage of the fluid relative to its production. As the outflow facility decreases, the IOP increases for a given aqueous humor production rate. Left untreated, an elevated IOP causes irreversible damage to the optic nerve and retinal fibers resulting in a progressive, permanent loss of vision.

The eye's ciliary body continuously produces aqueous humor, the clear fluid that fills the anterior segment of the eye (the space between the cornea and lens). The aqueous humor flows out of the anterior chamber (the space between the cornea and iris) through the canalicular (i.e., conventional) and the uveoscleral pathways, both of which contribute to the aqueous drainage system. Any impairment to the drainage of aqueous humor through these outflow pathways can influence the IOP of the eye.

FIG. 1 is a cross-sectional diagram of the front portion of an eye 10 that helps to explain the processes of glaucoma. In FIG. 1, representations of the lens 110, the lens capsule 112, the cornea 120, the iris 130, the ciliary body 140, the trabecular meshwork 150, Schlemm's canal 160, the collector channels 162, the anterior segment 165 including both the anterior chamber 170 and the posterior chamber 175, the posterior segment 178, the sclera 180, the retina 182, the choroid 185, the limbus 190, the suspensory ligaments or zonules 195, the suprachoroidal space 200, the conjunctiva 202, and the scleral spur 203 are pictured. Aqueous fluid is produced by the ciliary body 140, which lies beneath the iris 130 and adjacent to the lens 110 in the anterior chamber 170 of the anterior segment of the eye. This aqueous humor emerges from the ciliary processes 145, washes over the lens 110 and iris 130, and flows to the drainage systems located in the irideocorneal angle 204 (delineated by the dashed lines and bounded by the iris 130 and the cornea 120) of the eye 10.

After production by the ciliary body 140, the aqueous humor may leave the eye by several different routes. Some goes posteriorly through the vitreous body in the posterior segment 178 to the retina, while most circulates in the anterior segment 165 to nourish avascular structures such as the lens 110 and the cornea 120 before outflowing by two major routes located in the irideocorneal angle 204 of the eye 10: the trabecular or conventional trabecular outflow pathway 205 and the uveoscleral or nonconventional outflow pathway 210. The uveoscleral pathway 210 refers to the aqueous humor leaving the anterior chamber 170 by diffusion through intercellular spaces among ciliary muscle fibers. The trabecular outflow pathway 205 is the main route of outflow, accounting for a large percentage of aqueous egress. The route extends from the anterior chamber angle (formed by the iris 130 and the cornea 120), through the trabecular meshwork 150, into Schlemm's canal 160. The trabecular meshwork 150, which extends circumferentially around the anterior chamber 170, is commonly implicated in glaucoma. Among different types of glaucoma, most of those known as open-angle glaucomas are caused by an increase in the resistance to aqueous humor drainage through the trabecular meshwork and/or Schlemm's canal. The trabecular meshwork 150 seems to act like a filter, restricting the outflow of aqueous humor and providing a back pressure that directly relates to IOP. Schlemm's canal 160 is located just peripheral to the trabecular meshwork 150. Schlemm's canal 160 is fluidically coupled to the collector channels 162, thereby allowing aqueous humor to flow out of the anterior chamber 170 and into the bloodstream. After crossing the trabecular meshwork 150, the aqueous humor reaches Schlemm's canal 160 and the collector channels 162. The arrows A1 show the flow of aqueous humor from the ciliary muscle 140, over the lens 110, over the iris 130, through the trabecular meshwork 150, and into Schlemm's canal 160 and the collector channels 162 (to eventually reunite with the bloodstream in the aqueous veins 206 and episcleral vessels 207).

One method of treating glaucoma includes enhancing aqueous outflow. Several current treatments involve the use of ocular drainage implants that may lack long-term efficacy due to fibrosis at the drainage site or system malfunction. The system and methods disclosed herein overcome one or more of the deficiencies of the prior art.

SUMMARY

In one aspect, the present disclosure is directed to an extension device to extend ocular tissue within an irideocorneal angle of an eye of a patient, comprising a flexible body and a plurality of tensioning features disposed on the body. The body is sized and configured to be disposed within the irideocorneal angle. The body has a curved longitudinal axis, a channel extending from a first end to a second end, an inner convex side, and an outer concave side. The body is flexible between a first flexed condition and a second unflexed condition. The body has a first radius of curvature in the first flexed condition and a second radius of curvature in the unflexed condition. Each tensioning feature is shaped and sized to grasp the ocular tissue within the irideocorneal angle.

In one aspect, the first radius of curvature is smaller than the second radius of curvature. In another aspect, the second radius of curvature is smaller than the first radius of curvature.

In one aspect, the body has a curved, cylindrical, elongate shape. In another aspect, the body has an annular, open, generally circular shape.

In one aspect, each of the plurality of tensioning features comprises a slot-like opening extending from an inner surface to an outer surface of the body. In some instances, each slot-like opening assumes an open condition when the body assumes the first flexed condition and a closed condition when the body assumes the second unflexed condition.

In another aspect, each of the plurality of tensioning features comprises a hook extending from an inner surface to an outer surface of the body, the hook configured to pierce and retain ocular tissue.

In one aspect, the plurality of tensioning features are positioned on a central portion of the body. In another aspect, the plurality of tensioning features are positioned on peripheral portions of the body.

In one aspect, the plurality of tensioning features are positioned on the inner, concave side of the body. In another aspect, the plurality of tensioning features are positioned on the outer, convex side of the body.

In another exemplary aspect, the present disclosure is directed to a system designed to extend ocular tissue within an irideocorneal angle of an anterior chamber of an eye of a patient, comprising a flexible body, at least one tensioning feature disposed on the body, and a delivery instrument. In one aspect, the flexible body has a curved longitudinal axis, a channel extending from a first end to a second end, an inner convex side, and an outer concave side. The body is flexible between a first radius of curvature in a first flexed condition and a second radius of curvature in a second unflexed condition, and the body is sized and configured to be disposed within the irideocorneal angle. Each tensioning feature is shaped and sized to grasp the ocular tissue within the irideocorneal angle. The delivery instrument includes a push mechanism configured to advance the flexible body into the anterior chamber. In one aspect, the delivery instrument includes a guiding element that is removably coupled to the body and configured to constrain the curvature of the body when coupled to the body.

In another exemplary aspect, the present disclosure is directed to a method for extending trabecular meshwork in an eye. In one aspect, the method comprises forming an incision in the eye, inserting an extension device comprising tensioning features positioned on a flexible, curved body having a flexed condition and an unflexed condition into an anterior chamber, flexing the body of the extension device to assume a first radius of curvature, pushing the tensioning features against ocular tissue within an irideocorneal angle while the body is in a flexed condition, grasping the ocular tissues with the tensioning features, and unflexing the body to assume a second radius of curvature in the irideocorneal angle such that the tensioning features stretch the trabecular meshwork radially inward.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure. Throughout this description, like elements, in whatever embodiment described, refer to common elements wherever referred to and reference by the same reference number. The characteristics, attributes, functions, interrelations ascribed to a particular element in one location apply to that element when referred to by the same reference number in another location unless specifically stated otherwise. In addition, the exact dimensions and dimensional proportions to conform to specific force, weight, strength and similar requirements will be within the skill of the art after the following description has been read and understood.

All the figures are drawn for ease of explanation of the basic teachings of the present invention; the extensions of the FIGS. with respect to number, position, relationship and dimensions of the parts to form examples of the various embodiments will be explained or will be within the skill of the art after the following description has been read and understood.

FIG. 4A illustrates the trabecular meshwork, Schlemm's canal, and collector channels before extension, and FIG. 4B illustrates these tissues during extension.

FIG. 5 is a schematic diagram of an exemplary extension device disposed within the irideocorneal angle of an eye according to principles of the present disclosure.

FIG. 8A illustrates the exemplary extension device in a relaxed, unconstrained condition, and FIG. 8B illustrates the exemplary extension device in a flexed, constrained condition.

FIG. 9A illustrates the exemplary extension device in a flexed, constrained condition (e.g., during implantation of the device), and FIG. 9B illustrates the exemplary extension device in an unconstrained condition (e.g., post-implantation).

FIG. 11A illustrates the exemplary extension device in a flexed, constrained condition, and FIG. 11B illustrates the exemplary extension device in a relaxed, unconstrained condition.

FIG. 13A illustrates the exemplary extension device in a flexed, constrained condition, and FIG. 13B illustrates the exemplary extension device in a relaxed, unconstrained condition.

FIG. 15A illustrates the exemplary extension device in a flexed, constrained condition, and FIG. 15B illustrates the exemplary extension device in a relaxed, unconstrained condition.

DETAILED DESCRIPTION

Figure 1:
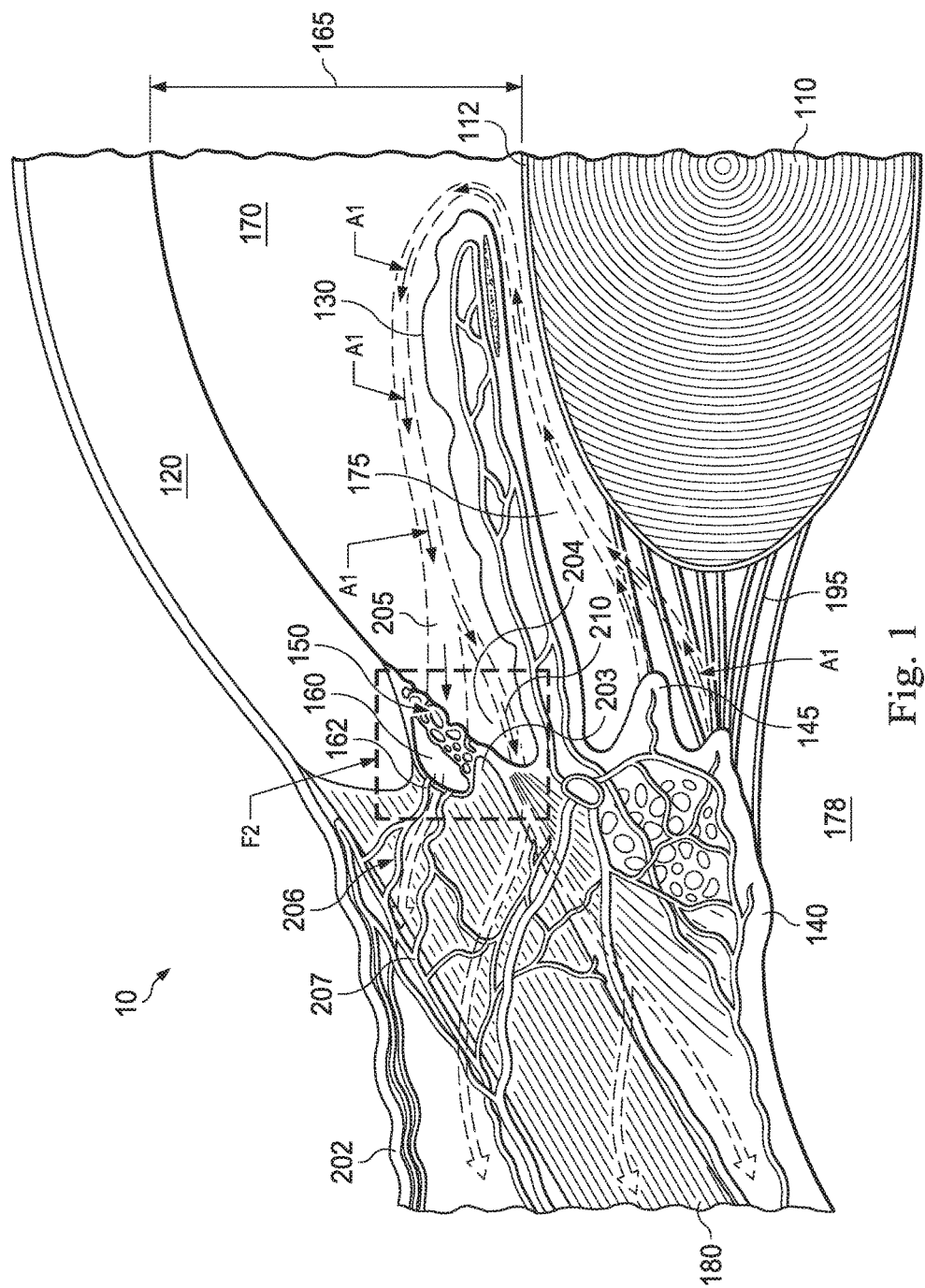
FIG. 1 is a cross-sectional diagram illustrating the front portion of an eye.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

The present disclosure is directed to devices and methods of drainage of fluid (e.g., aqueous humor from the anterior chamber 170) for treating a medical condition, such as glaucoma. In one aspect, the devices and systems described herein adjusts IOP by enhancing fluid drainage through a natural outflow path of aqueous humor, the trabecular outflow pathway 205. In particular, the devices described herein are shaped and configured to extend or stretch at least a portion of the trabecular meshwork 150 radially toward the center of the anterior chamber 170 (i.e., towards the center of the iris 130). By physically tugging all or a portion of the trabecular meshwork 150 toward the center of the anterior chamber 170, the devices disclosed herein spread the cellular layers of the trabecular meshwork 150, thereby decreasing the resistance to aqueous humor outflow. Thus, the devices and systems act to enhance fluid drainage from the anterior segment 165 of an eye 10 through the trabecular outflow pathway 205.

Figure 2:
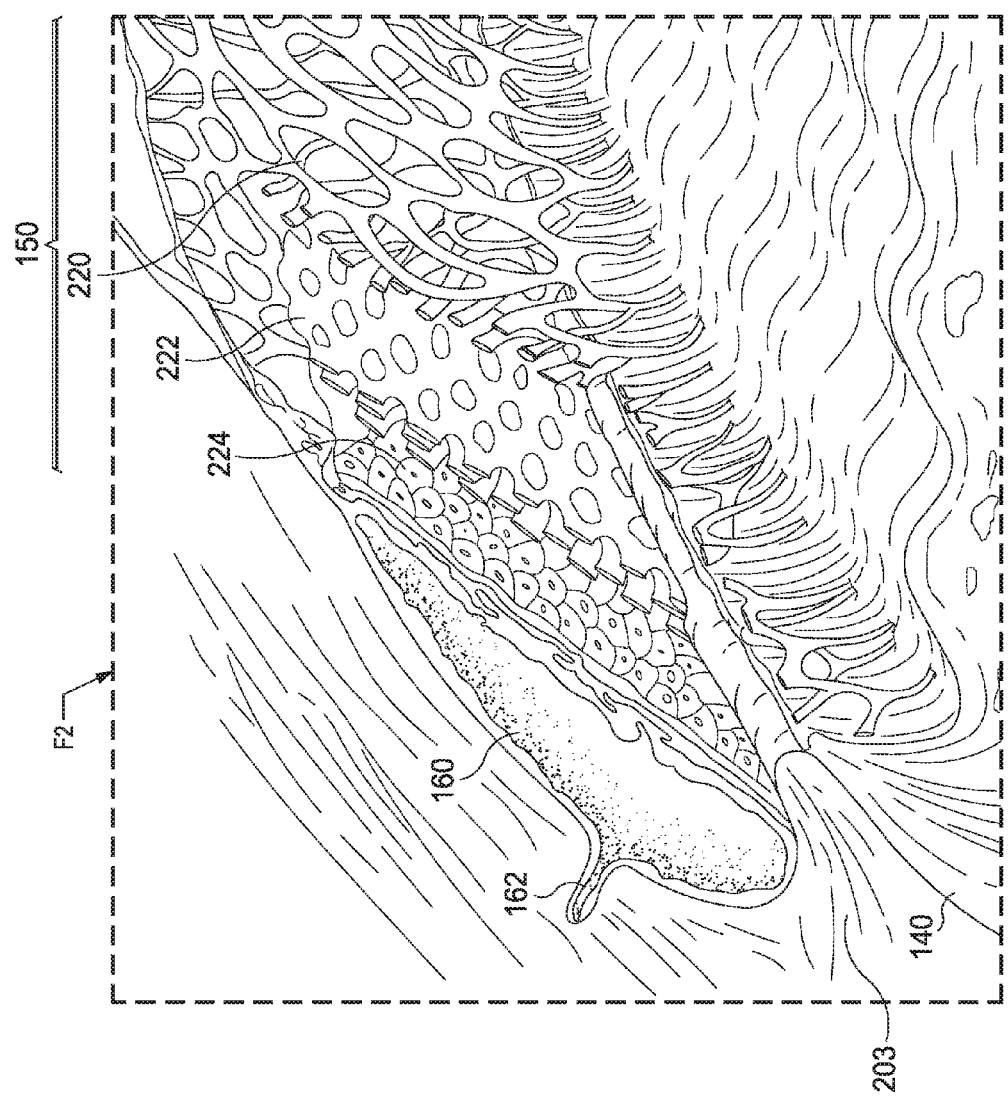
FIG. 2 is a more detailed illustration of the irideocorneal angle and associated ocular structures shown in FIG. 1, including a cutaway view of the layers of the trabecular meshwork (within box F2).

FIG. 2 is a detailed illustration of the irideocorneal angle and associated ocular structures indicated by the box labeled F2 in FIG. 1, including a cutaway view of the layers of the trabecular meshwork 150. As mentioned above, the main outflow route for aqueous humor in the human eye 10 is the trabecular or conventional trabecular outflow pathway 205. On this route, aqueous humor exits the eye 10 through the trabecular meshwork (TM) in an IOP-dependent manner. In particular, FIG. 2 illustrates the three differentiated layers of the trabecular meshwork 150: the uveal meshwork 220, the corneoscleral meshwork 222, and the juxtacanalicular meshwork 224. From the inner to the outermost part, the layer of tissue closest to the anterior chamber 170 is the uveal meshwork 220, formed by prolongations of connective tissue arising from the iris 130 and ciliary body 140 and covered by endothelial cells. This layer may not offer much resistance to aqueous humor outflow because intercellular spaces are large. The next layer, known as the corneoscleral meshwork 222, is characterized by the presence of lamellae covered by endothelium-like cells standing on a basal membrane. The lamellae are formed by glycoproteins, collagen, hyaluronic acid, and elastic fibers. The higher organization of the corneoscleral meshwork 222 compared to the uveal meshwork 220 as well as the narrower intercellular spaces are largely responsible for the increase in flow resistance. The third layer, the juxtacanalicular meshwork 224, is in direct contact with the inner wall of endothelial cells from Schlemm's canal 160. The juxtacanalicular meshwork 224 is formed by cells embedded in a dense extracellular matrix, and the majority of the tissue resistance to flow supposedly lies in this layer, due to its narrow intercellular spaces. The layer of endothelial cells from Schlemm's canal 160 is the last barrier that aqueous humor has to cross before exiting the eye through the trabecular outflow pathway 205. The extension devices described herein may be shaped and configured to grasp any or all of the layers of the trabecular meshwork 150.

The ligamentous insertions of the ciliary muscle 140 in the trabecular meshwork 150 modulate the permeability of the trabecular meshwork 150 to aqueous humor. When the ciliary muscle 140 contracts, its muscular insertions cause widening of the intercellular spaces in the trabecular meshwork 150, thereby increasing the permeability of the tissue. Simultaneously, outflow of aqueous humor through the uveoscleral pathway 210 may decrease. In the opposite scenario, when the ciliary muscle 140 relaxes, the intercellular spaces of the trabecular meshwork 150 become narrower, the outflow through the trabecular outflow pathway 205 is reduced, and the uveoscleral flow is increased. In accordance with this observation, drugs mimicking parasympathetic nerve stimulation (e.g., pilocarpine), which contracts the ciliary muscle 140 (widening the trabecular meshwork 150 through increased tension on the scleral spur 203), increase the amount of aqueous humor drained through the trabecular outflow pathway 205. Therefore, the aqueous humor outflow is generally distributed between the trabecular outflow pathway 205 and the uveoscleral pathway 210, depending on the tone of the ciliary muscle 140.

Figure 3:
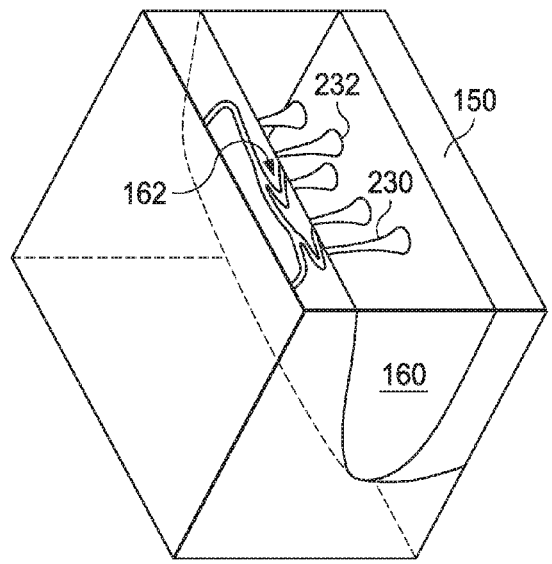
FIG. 3 is a diagrammatic illustration of the relationship between the trabecular meshwork and Schlemm's canal.

Thus, by tugging the trabecular meshwork 150 inward toward the center of the anterior chamber 170, the devices described herein mimic the effect of ciliary muscle contraction on the trabecular meshwork 150 by widening the intercellular spaces in the tissue, thereby decreasing the resistance to aqueous humor outflow. Another way in which the devices described herein facilitate aqueous humor outflow is by opening collector channel ostia. FIG. 3 illustrates the relationship between the trabecular meshwork 150, Schlemm's canal 160, and the collector channels 162. FIG. 3 is a diagrammatic illustration of the trabecular meshwork 150, Schlemm's canal 160, and the collector channels 162. As the devices described herein physically stretch the layers of trabecular meshwork 150 radially inward, the trabecular meshwork 150 simultaneously pulls the connective tissue within Schlemm's canal 160. This connective tissue forms elastic tubes 230 connecting S-shaped, valve-like or flap-like collector channel ostia 232 with the trabecular meshwork 150. In particular, by tugging on the trabecular meshwork 150, the devices described herein decrease the resistance to aqueous humor outflow by pulling open the collector channel ostia 232 by inducing tension on the elastic tubes 230 disposed between the trabecular meshwork 150 and the collector channels 162. Extension of the trabecular meshwork 150 causes the elastic tubes 230 to pull open the flap-like collector channel ostia 232 to allow aqueous humor to more easily flow into the collector channels 162.

Figure 4A:
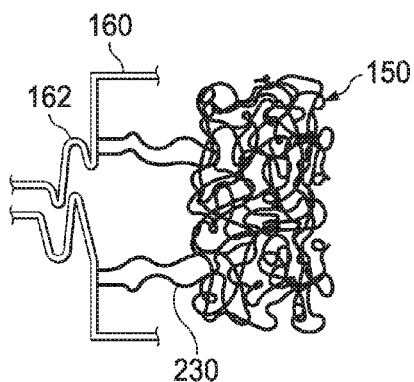
FIGS. 4A and 4B are schematic diagrams illustrating the effect of physical extension of the trabecular meshwork on the associated ocular tissues.
Figure 4B:
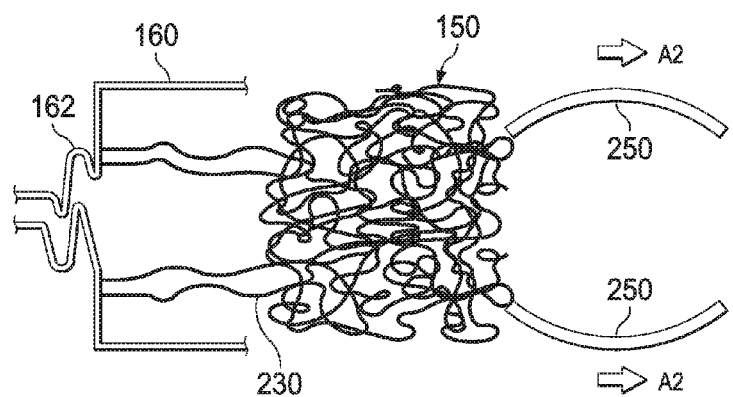

FIGS. 5A and 5B are schematic diagrams illustrating the effect of physical extension of the trabecular meshwork 150 on the associated ocular tissues. FIG. 4A illustrates the trabecular meshwork 150, Schlemm's canal 160, and collector channels 162 before extension, and FIG. 4B illustrates these tissues during extension in the direction of arrows A2. FIG. 4B illustrates a cross-sectional diagram of an exemplary extension device 250 engaging the trabecular meshwork 150. In particular, FIG. 4B illustrates the stretching or extension of the trabecular meshwork 150, as well as the subsequent stretching of the elastic tubes 230 within Schlemm's canal 160, and the resultant expansion of Schlemm's canal 160 and the collector channels 162. In FIG. 4A, there is more resistance to aqueous outflow, and in FIG. 4B, there is less resistance to aqueous outflow (e.g., by increasing the surface area of the trabecular meshwork 150). In some embodiments, the same effect may be achieved if the extension device 250 is shaped and configured to grasp either the iris 130 or the ciliary muscle 140 within the irideocorneal angle 204 (i.e., in the region delineated by the box F2 in FIG. 1). In some embodiments, the extension device 250 may be coupled to an intraocular lens ("IOL").

FIG. 5 is a schematic diagram of the exemplary extension device 250 disposed within the irideocorneal angle 204 of the eye 10 according to principles of the present disclosure. In the pictured embodiment, the extension device 250 comprises curved, hollow, cylindrical body 252, which includes inner apertures 255 and end apertures 260.

In the situation pictured in FIG. 5, the extension device 250 is positioned and self-retaining in irideocorneal angle 204 of the eye 10 such that aqueous humor from the anterior chamber 170 flows through the inner apertures 255 and the end apertures 260 of the extension device 250 into the trabecular meshwork 150 and then through Schlemm's canal 160 (and then through the remainder of the trabecular outflow pathway 205, including the collector channels 162 and the blood vessels, as described above). The fluid flow from the anterior chamber 170 through the extension device 250 and into the trabecular meshwork 150 may be determined by pressure differentials across the extension device 250 and the degree of stretching of the trabecular meshwork 150 achieved by the extension device 250. According to the principles of the present disclosure, the greater the amount of radially inward extension of the trabecular meshwork 150 achieved by the extension device 250, the easier and possibly the greater the fluid outflow through the trabecular outflow pathway 205.

Figure 6A:
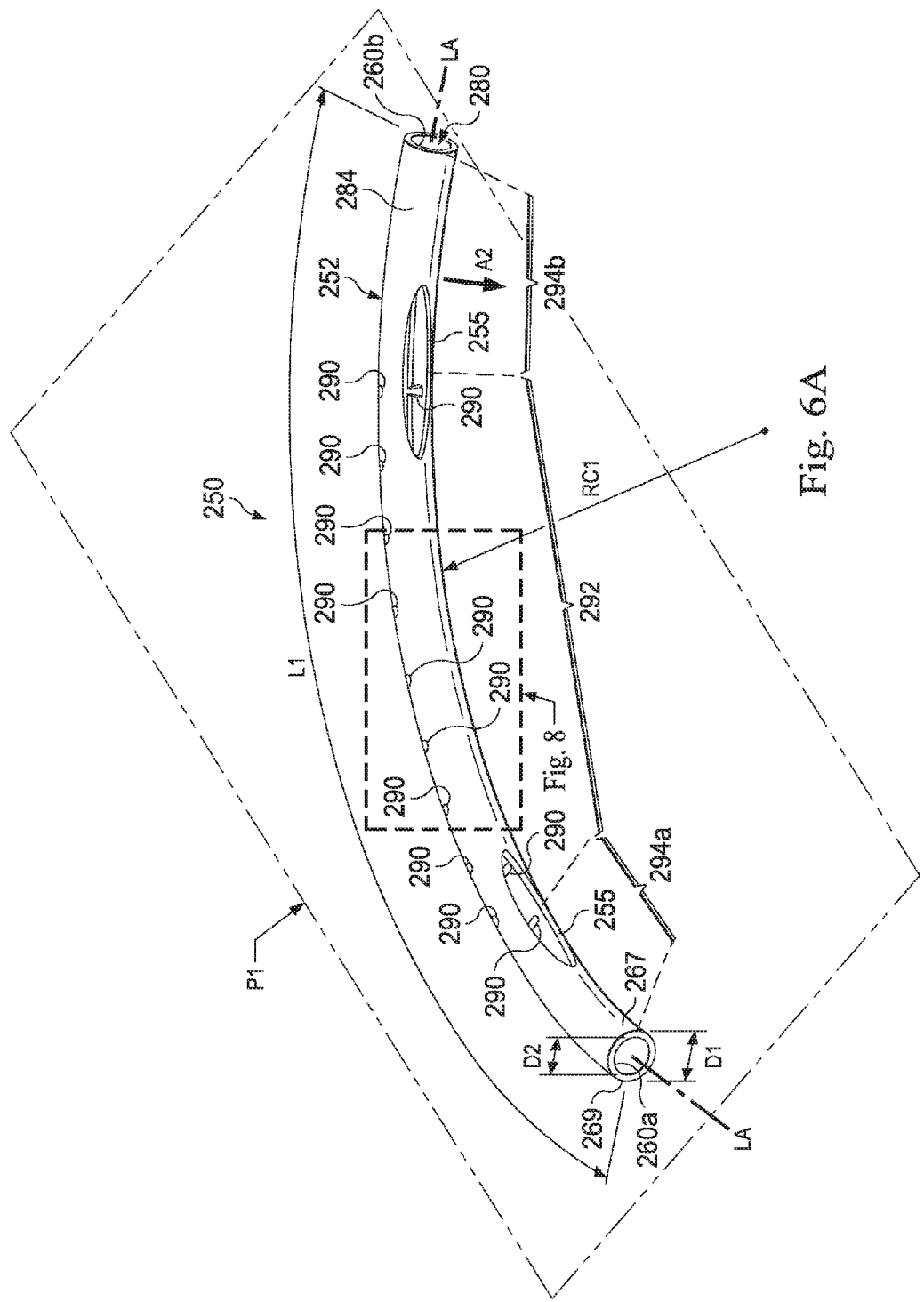
FIG. 6A is a perspective view of an exemplary extension device according to one embodiment of the present disclosure, illustrating a front aspect of the exemplary extension device.
Figure 6B:
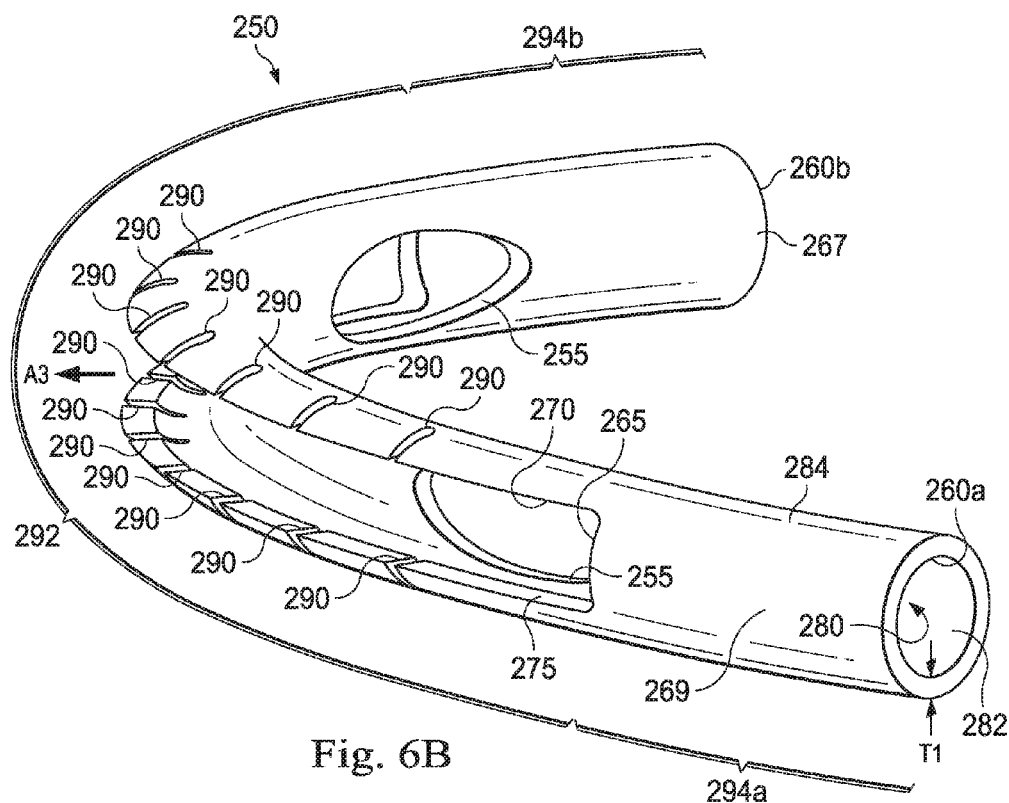
FIG. 6B is another perspective view of the exemplary extension device shown in FIG. 6A, illustrating side and back aspects of the exemplary extension device.
Figure 7:
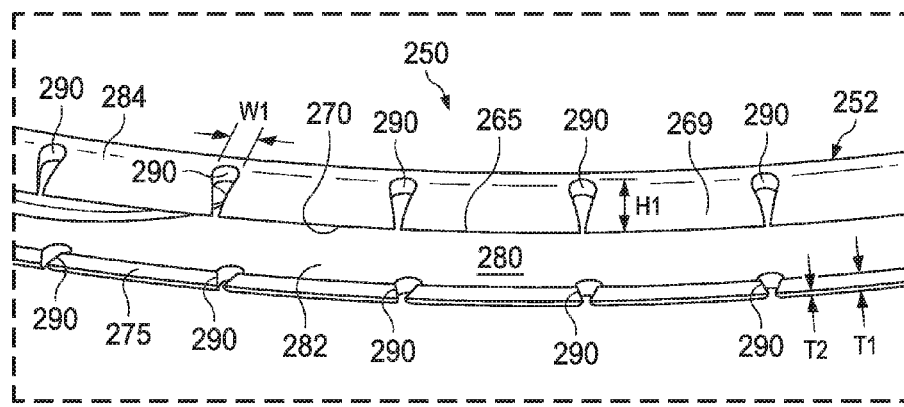
FIG. 7 is a perspective view of a portion of the exemplary extension device shown in FIG. 6A, illustrating a back aspect of the exemplary extension device.

FIG. 6A is a perspective view of a front aspect of the extension device 250. FIG. 6B is a perspective view of side and back aspects of the extension device 250 shown in FIG. 6A. FIG. 7 is an enlarged view of a back aspect of the central portion of the extension device 250 shown in the box F8 of FIGS. 6A and 6B.

The body 252 of the extension device 250 is a hollow, slightly flexible, cylindrical rod that extends along a generally curved longitudinal axis LA from a first end aperture 260a to a second end aperture 260b. The end apertures 260a, 260b of the extension device 250 have atraumatic shapes configured with blunt edges to prevent inadvertent injury to ocular tissues during implantation or if the extension device 250 moves after implantation. In some embodiments, the blunt edges of the end apertures 260a, 260b may be shaped in an atraumatic manner by having a rounded profile. In some embodiments, the blunt edges of the end apertures 260a, 260b may be manufactured of or be coated with a soft material.

The extension device 250 includes an arc length L1 extending from the first end aperture 260a to the second end aperture 260b. The arc length L1 may range from 4.0 mm to 36.0 mm. In some embodiments, the arc length L1 measures 9.0 mm. The extension device 250 may have an angular span ranging from 40° to 360°. For example, in one embodiment, the extension device 250 has an angular span of 90°. The extension device 250 is shown as an arcuate tube, but in other embodiments, the extension device may comprise a circular tube shaped and configured to encircle the entire iris when implanted in the irideocorneal angle 204. Such embodiments may lack end apertures 260 and include more inner apertures 255. In such embodiments, the arc length L1 approximates the circumference of the iris 130 and/or the irideocorneal angle 204. The longitudinal axis LA lies on a plane P1 along the entire length L1 of the body 252 of the extension device 250. In other embodiments, the extension device 250 may be sized to occupy more or less of the irideocorneal angle 204.

The body 252 has a plurality of inner apertures 255, two end apertures 260a, 260b, and an outer aperture 265. In the pictured embodiment, the body includes two inner apertures 255, but other embodiments may include more or less apertures provided that the extension device 250 includes sufficient inner apertures 255 to ensure adequate drainage of aqueous humor through the extension device 250 and into the trabecular meshwork 150. Some embodiments may lack inner apertures. For example, an extension device 250 having a longer arc length L1 may include more inner apertures 255, and an extension device 250 having a shorter arc length L1 may include fewer inner apertures 255. Although the two terminal ends of the extension device 250 are described as end apertures 260a, 260b, some embodiments may lack end apertures 260a, 260b and the body 252 may extend from a first closed end to a second closed end.

FIG. 6B demonstrates that the extension device includes at least one outer aperture 265 in addition to the inner apertures 255 and the end apertures 260a, 260b. Whereas the inner apertures 255 are disposed on an inner side 267 of the extension device 250, the outer aperture 265 is disposed on an outer side 269 of the extension device 250. The outer aperture 265 is formed as a wide slot-like opening defined by a first edge 270 and a second edge 275. The outer aperture 265, the end apertures 260a, 260b, and the inner apertures 255 all fluidly communicate with an elongate channel 280, which extends through the body 252 from the end aperture 260a to the end aperture 260a and is defined by an inner surface 282 of the body 252. Thus, when implanted as shown in FIG. 5, the inner apertures 255 open in a radially inward direction toward the center of the anterior chamber 170 as indicated by arrow A2 (as shown in FIG. 6A), and the outer aperture 265 opens in a radially outward direction toward the trabecular meshwork 150 as indicated by the arrow A3 (shown in FIG. 6B).

It should be noted that the spatial configuration, size, and angle of the apertures may vary in different embodiments. Various embodiments of the extension device 250 may include any number and arrangement of apertures that communicate with the elongate channel 280. Multiple apertures in the extension device 250 guard against the blockage of flow through the extension device 250 in instances where other apertures may be blocked. In the embodiment shown in FIG. 6A, the apertures (e.g., inner apertures 255) are arranged in a symmetrical pattern along inner surface 282 of the body 252. In other embodiments, however, the apertures may be arranged in any of a variety of patterns, both asymmetrical and symmetrical, along any portion (or entirety) of the body 252. In some embodiments, the apertures may also function as visual markers to aid in positioning the extension device 250 within the eye 10. Any or all of the apertures may include blunt or atraumatic edges designed to minimize or prevent injury to the neighboring ocular tissues.

As shown in FIG. 6A, the extension device 250 includes an outer diameter D1. The extension device 250 has peripheral dimensions sized to be equal to or smaller than the diameter of the irideocorneal angle 204 (i.e., smaller than the diameter of the shallow canal formed at the intersection of the cornea 120 and the iris 130). In some embodiments, as shown in FIG. 5, the peripheral dimensions of the extension device 250 are sized such that the extension device 250 fits snugly in the irideocorneal angle 204 without causing undue trauma to the neighboring ocular tissues, thereby preventing or minimizing fibrosis in response to the implant. The outer diameter D1 may range from 0.25 mm to 1.5 mm. In some embodiments, the outer diameter D1 measures 0.75 mm. As mentioned above, the body 252 of the extension device 250 defines the elongate channel 280. The elongate channel 280 includes an inner diameter D2. The inner diameter D2 may range from 0.15 mm to 1.4 mm. In some embodiments, the inner diameter D2 measures 0.25 mm. Other diameters are contemplated. As shown in FIG. 6A, in some embodiments the extension device 250 has a substantially uniform outer diameter D1 and a substantially uniform inner diameter D2 along the entire length L1. In other embodiments the dimensions of the extension device 250, including the outer diameter D1 and/or the inner diameter D2, may vary along the length L1.

As shown in FIG. 6B, the body 252 includes a first wall thickness T1 extending from the inner surface 282 to an outer surface 284. The first wall thickness T1 may range from 0.05 mm to 0.25 mm. In some embodiments, the first wall thickness T1 measures 0.1 mm. In some embodiments, the extension device 250 has a single wall thickness (e.g., the first wall thickness T1) throughout the body 252. In other embodiments, the wall thickness varies at different regions of the body 252. For example, as best shown in FIG. 7, the wall thickness may taper from a first wall thickness T1 to a second wall thickness T2 at the second edge 275 of the body 252. The second wall thickness T2 may range from 0.0 mm to 0.25 mm. In some embodiments, the second wall thickness T2 measures 0.05 mm. Other dimensions are contemplated.

Although the extension device 250 is shown having a circular cross-sectional shape, the extension device 250 may have any of a variety of cross-sectional shapes, including without limitation, an ovoid or elliptical shape. In some embodiments, the extension device 250 may vary in cross-sectional shape along its length. The particular cross-sectional shape may be selected to facilitate easy insertion into the irideocorneal angle 204 of the anterior chamber 170 of the eye 10, and may be dependent upon the method of insertion planned. In some embodiments, the particular cross-sectional shape may be selected to facilitate drainage through the extension device 250. For example, a particular cross-sectional shape may help create a pressure gradient that may help fluid and/or particulate matter that may otherwise clog the extension device 250 to progress through the inner apertures 255 and exit through the outer aperture 265 into the trabecular meshwork 150. In some embodiments, the particular cross-sectional shape may be selected to facilitate self-retention within the eye 10 (e.g., within the irideocorneal angle 204).

The extension device 250 described herein may be flexible along its entire length. In particular, the body 252 may have a predetermined level of flexibility or stiffness along its entire length, or may have a varying degree of flexibility or stiffness along its length. The flexibility of the body 252 is at a maximum when the body 252 is bending along the first plane P1 shown in FIG. 6A, and the body 252 has less flexibility and is relatively more rigid when bending along any plane other than the first plane P1. The extension device 250 may be made from any of a variety of flexible, rigid, or composite materials. The extension device 250 described herein may be made from any of a variety of biocompatible materials having the requisite flexibility and hoop strength for adequate flexibility to open the tensioning features 290 during implantation, in addition to adequate lumen support and drainage through the inner apertures 255 after implantation. The extension device 250 is constructed from a structurally deformable biocompatible material that can elastically or plastically deform without compromising its integrity. The extension device 250 may be made from a self-expanding biocompatible material, such as Nitinol or a resilient polymer, or an elastically compressed spring temper biocompatible material. Other materials having shape memory characteristics, such as particular metal alloys, may also be used. Possible materials include, without limitation, silicone, silicone polyimide, polycarbonate, polymethylmethacrylate (PMMA), nylon, prolene, polyurethane, silastic, polyamide or a combination thereof, or any other biocompatible material having the requisite properties of resilience, flexibility, and suitability for use in ophthalmic procedures. The shape memory materials allow the extension device 250 to be restrained in a low profile configuration during delivery into the eye 10 and to resume and maintain its expanded shape in vivo after the delivery process. The material composition of the extension device 250 resiliently biases the body 252 toward the expanded condition. In particular, in this example, the extension device 250 is formed of an elastic material allowing the body 252 to elastically deform to an unexpanded state to facilitate delivery through small incision (e.g., through a tubular delivery instrument), and spring back to an expanded state as it enters the eye 10. In other embodiments, the extension device 250 may be made of a shape memory alloy having a memory shape in the expanded configuration.

In some instances, the extension device 250 may be scored or otherwise imprinted (in addition to the tensioning features 290 described below) for added flexibility throughout the tube or only in one or more portions of the extension device 250. In the pictured embodiments, as shown in FIG. 6A, the extension device 250 includes a radius of curvature RC1 that is slightly higher than the radius of curvature of the irideocorneal angle 204 or, more specifically, the radius of curvature of the anterior chamber corner. In some embodiments, the body 252 may have a predetermined radius of curvature RC1 that conforms to the radius of curvature desirable to most securely self-retain the extension device 250 within the irideocorneal angle 204 or other location within the anterior chamber 170. In other embodiments, the extension device 250 may be sufficiently flexible to conform to the shape of a canal or hollow that may have been created between the cornea 120 and the iris 130 (e.g., post-trabectome procedure).

The extension device 250 may be coated with any of a variety of biocompatible materials, including, by way of non-limiting example, polytetrafluoroethylene (PTFE). The body 252 of the extension device 250 may be coated on its inner surface 282 with one or more drugs or other materials designed to help maintain the patency of the elongate channel 280 and the apertures (e.g., the end apertures 260a, 260b, the inner apertures 255, and/or the outer aperture 265). Likewise, any of the embodiments of the extension device 250 described herein may be coated on its outer surface 284 with one or more drugs or other materials designed to encourage healing and/or in-growth of ocular tissue around the extension device 250 to assist in retention of the extension device 250 (e.g., within the irideocorneal angle 204) or to prevent an immune response to the extension device 250. Such drugs or other materials may also or in the alternative be contained within a polymeric coating applied to the extension device 250.

As best shown in FIG. 7, the extension device 250 includes a plurality of tensioning features 290. The tensioning features 290 are configured to engage with the surrounding tissue (e.g., the trabecular meshwork 150, the scleral spur 203, the ciliary muscle 140, and/or the iris 130) to extend or stretch the trabecular meshwork 150 and associated downstream ocular structures (i.e., Schlemm's canal 160, the elastic tubes 230 or connective tissue, and/or the collector channels 162) radially inward toward the center of the iris 130. In some embodiments, the tensioning features 290 may function as visual markers to aid in positioning the extension device 250 within the eye 10. In addition, the tensioning features 290 may minimize inadvertent movement of the extension device 250 after implantation. Thus, the tensioning features 290 extend the trabecular meshwork 150 and may aid in proper retention of the extension device 250 within the eye 10 after implantation. As shown in FIG. 5, the extension device 250 is shaped and configured to be implanted in the anterior chamber 170 within the irideocorneal angle 204 between the trabecular meshwork 150 and the iris 130. The extension device 250 may be held in place within the eye 10 via the surrounding anatomy, a spring force, and the tensioning features 290, all of which may stabilize the extension device 250 relative to the patient's eye 10.

In the exemplary embodiment shown in FIGS. 6-8B, the tensioning features 290 are located in a central portion 292 of the body 252 and comprise slots or cutouts in the first edge 270 and the second edge 275. Terminal portions 294a, 294b of the extension device 250 lack the tensioning features 290. The tensioning features 290 extend through the body 252 from the outer surface 284 to the inner surface 282 of the extension device 250. In the pictured embodiment of FIG. 7, the extension device 250 is in an unconstrained condition, and the tensioning features 290 comprise teardrop-shaped slots (i.e., when the extension device is in a generally native or relaxed condition). As shown in FIG. 7, the tensioning features 290 include a height H1 and a base width W1. The height H1 may range from 0.1 mm to 0.3 mm. In one example, the height H1 measures 0.2 mm. The base width W1 may range from 0.02 mm to 0.2 mm. In one example, the base width W1 measures 0.1 mm. Other dimensions are contemplated. Although the tensioning features 290 shown in FIG. 7 are substantially identical in size and shape, other embodiments may include tensioning features 290 of varying sizes and shapes.

It should be noted that the shape, spatial configuration, size, and angle of the tensioning features 290 may vary in different embodiments. For example, in other embodiments, the tensioning features 290 may comprise slots having any of a variety of shapes, including without limitation, rectangular, ovoid, cyclic, round, or combinations thereof. In the embodiment shown in FIG. 6A, the tensioning features 290 are distributed in a symmetrical pattern along the body 252 of the extension device 250 on both the first and second edges 270, 275. In other embodiments, however, the tensioning features 290 may be arranged in any of a variety of patterns, both asymmetrical and symmetrical, along any portion (or entirety) of the extension device 250. In yet other embodiments, as described below with reference to FIGS. 10A, 12A, and 15, the tensioning features need not comprise slots, and may comprise any of a variety of other structures, including without limitation, protrusions such as hooks, nubs, ribs, prongs, textured surfaces, and indentations.

Figure 8A:
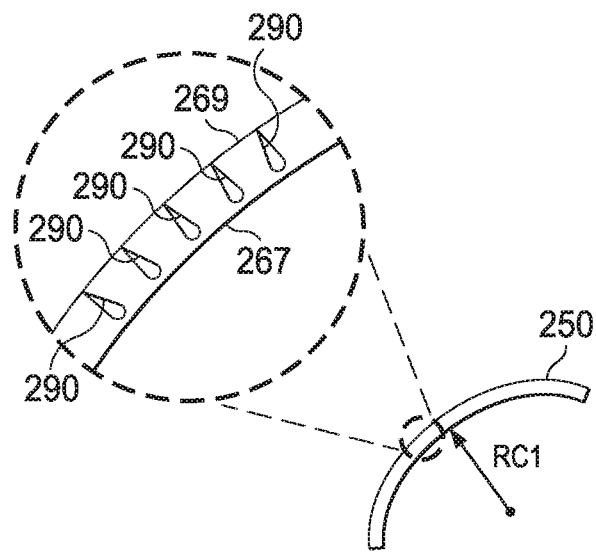
FIGS. 8A and 8B are diagrammatic illustrations of a portion of the exemplary extension device shown in FIG. 6A according to principles of the present disclosure.
Figure 8B:
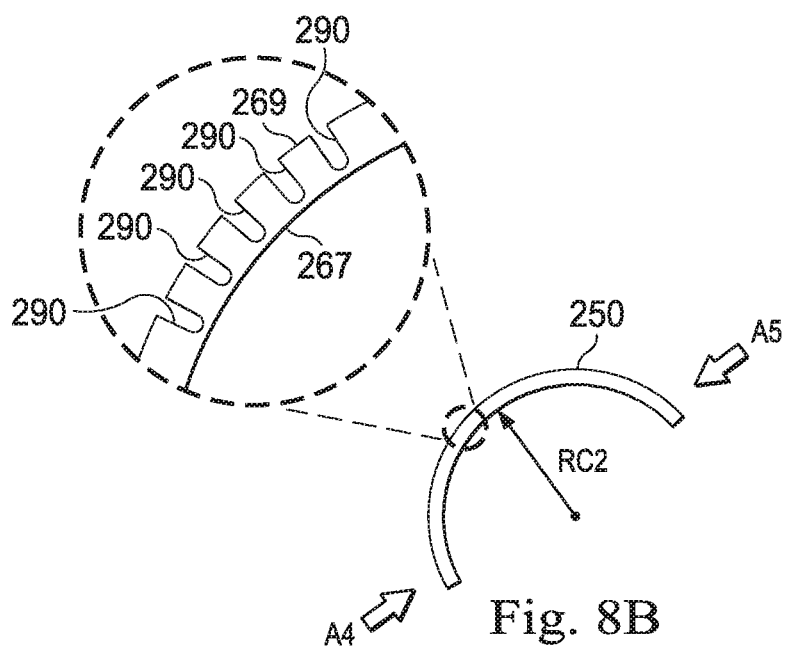

FIG. 8A illustrates the extension device 250 in a relaxed, unconstrained condition, and FIG. 8B illustrates the extension device 250 in a flexed, constrained condition. In various embodiments, the tensioning features 290 are flexible in that they change in shape as the extension device 250 transitions between a native, relaxed, and unconstrained condition (i.e., the closed condition shown in FIG. 8A) and a flexed and constrained condition (i.e., the open condition shown in FIG. 8B). The body 252 is formed with a predetermined radius of curvature RC1, as shown in FIG. 8A. In a relaxed or un-flexed state, the tensioning features 290 of the extension device 250 are in a closed condition as shown in FIG. 8A. When force is applied to the ends of extension device 250 in the direction of arrows A4 and A5, as shown in FIG. 8B, the body 252 flexes to assume a smaller radius of curvature RC2, causing the tensioning features 290 assume an open condition. The arrows A4, A5 are on or parallel to the first plane P1 (shown in FIG. 6A) that intersects the longitudinal axis LA along the entire length L1 of the body 252 of the extension device 250. The structure of the body 252 is such that the tensioning features 290 are biased to transition from the open condition shown in FIG. 8B during initial positioning in the eye 10 (i.e., when the extension device is in a flexed condition) to the closed condition shown in FIG. 8A after final implantation of the extension device 250 within the irideocorneal angle 204 (i.e., when the extension device is in a relatively unconstrained and un-flexed condition).

Figure 9A:
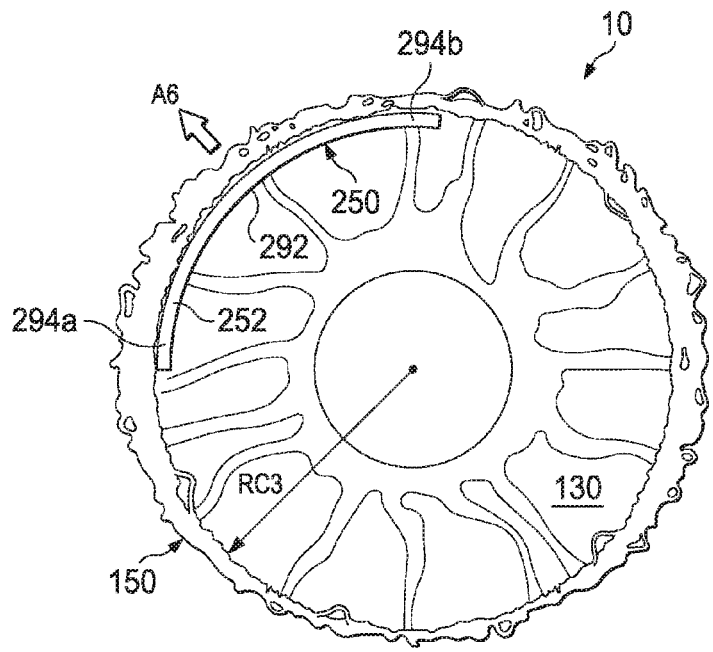
FIGS. 9A and 9B are diagrammatic illustrations of the exemplary extension device shown in FIG. 6A positioned within an eye.
Figure 9B:
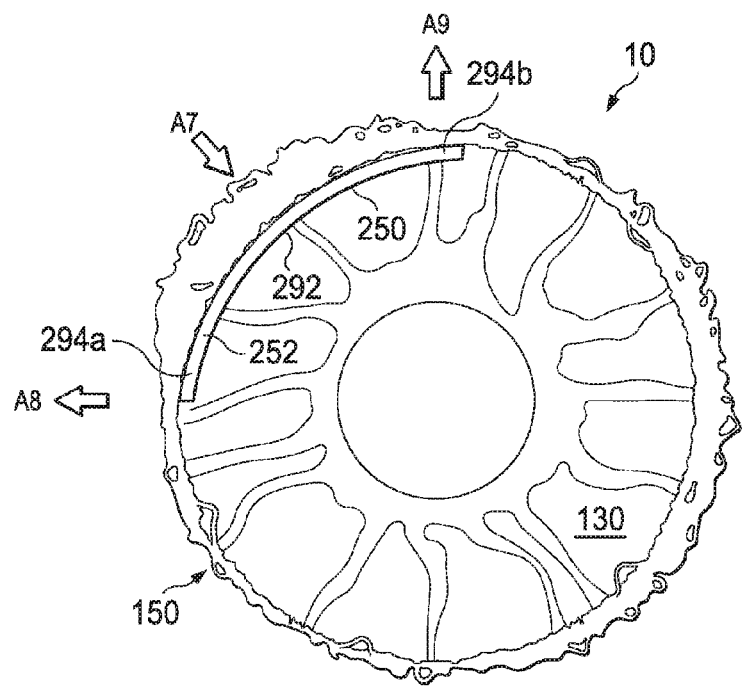

FIGS. 9A and 9B are diagrammatic illustrations of the extension device shown in FIGS. 6A-8B positioned within the eye 10. FIG. 9A illustrates the extension device 250 in a flexed, constrained condition (e.g., during implantation of the device), and FIG. 9B illustrates the extension device in an unconstrained condition (e.g., post-implantation). During implantation into the eye 10, the extension device 250 is flexed or bent into a flexed condition while being initially positioned in the irideocorneal angle 204 between the trabecular meshwork 150 and the iris 130. The tensioning features 290 of the extension device 250 may be positioned to engage the trabecular meshwork 250, the base or root of the iris 130, and/or the scleral spur 203. In FIG. 9A, the extension device 250 is in a flexed condition such that the body 252 has a smaller radius of curvature RC2, as shown in FIG. 8B. As mentioned above with respect to FIG. 8B, when the extension device 250 is in a flexed condition, the teardrop-shaped tensioning features 290 assume an open condition. In particular, the extension device 250 may be flexed or constrained to assume a radius of curvature RC2 that is equal to or smaller than a radius of curvature RC3 of the irideocorneal angle 204 (or anterior chamber corner) of the eye 10. While the tensioning features 290 are in an open condition, the surgeon (or other healthcare professional) can gently push the flexed extension device 250 into the irideocorneal angle 204 (e.g., into the trabecular meshwork 150) in the direction of arrow A6. As the central portion 292 of the extension device 250 is pushed into ocular tissue, portions of the ocular tissue gather into the open tensioning features 290.

After correctly positioning the extension device 250 in a region of the trabecular meshwork 150 with neighboring collector channels 162, the surgeon unflexes and releases the extension device 250, thereby causing the extension device 250 to regain the larger radius of curvature RC1 and the tensioning features 290 to assume a closed condition, as shown in FIG. 8A, around the gathered ocular tissue. As shown in FIG. 9B, when the extension device 250 is released and assumes a relaxed or un-flexed condition, the tensioning features 290 of the extension device 250 close to grasp the trabecular meshwork 150 and stretch the trabecular meshwork 150 radially inward in the direction of arrow A7. As the trabecular meshwork 150 is pulled radially inward, the effective surface area of the trabecular meshwork 150 increases, thereby decreasing resistance to the outflow of aqueous humor. It is important to note that while the trabecular meshwork 150 is pulled radially inward by the central portion 295 of the body 252 containing the tensioning features 290, the two terminal portions 294a, 294b of the body 252 compress the trabecular meshwork 150 radially outward in the directions of arrows A8, A9, respectively. Thus, the tensioning features 290 at the central portion 292 of the body 252 allow the extension device 250 to self-retain in the eye 10, while tugging the trabecular meshwork 150 radially inward toward the center of the iris 130, and the terminal portions 294a, 294b (i.e., the tips of the extension device 250) push radially outward into the trabecular meshwork 150 to balance the force and stabilize the device 250.

Figure 10A:
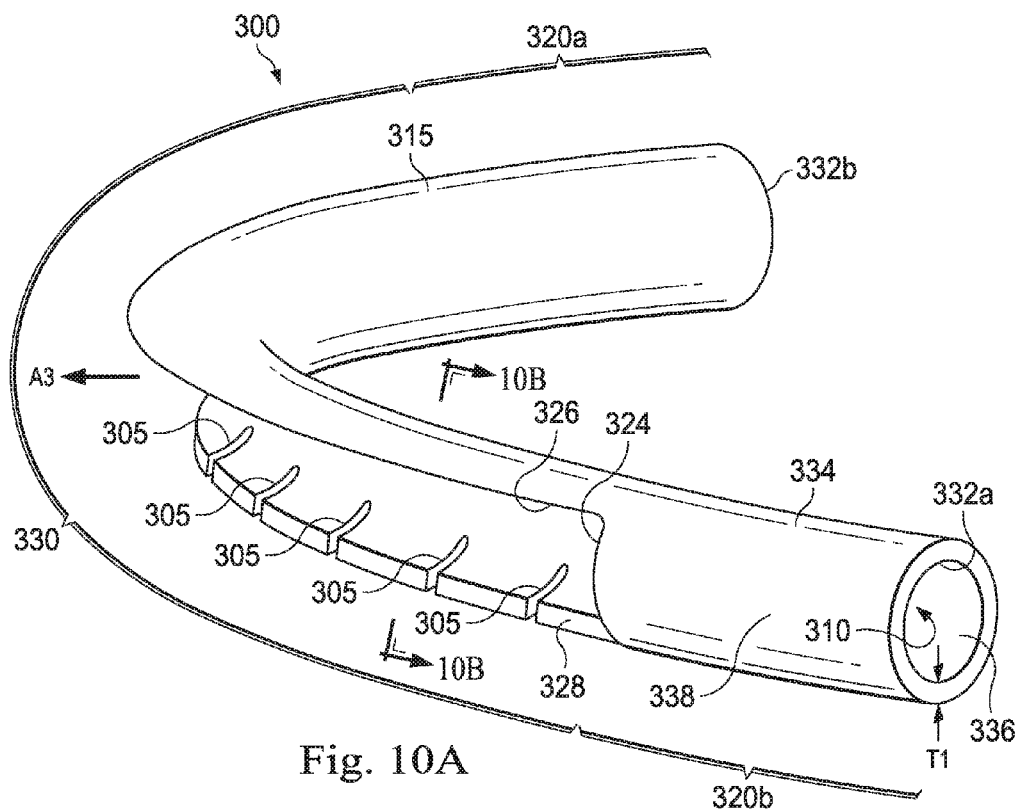
FIG. 10A is a perspective view of an exemplary extension device according to one embodiment of the present disclosure, illustrating a front aspect of the exemplary extension device.
Figure 10B:
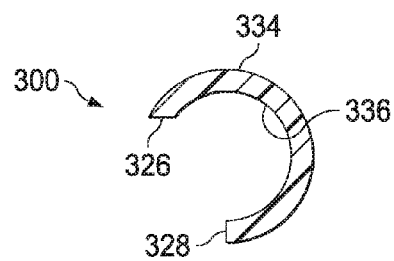
FIG. 10B is a cross-sectional view of the exemplary extension device shown in FIG. 10A.

FIG. 10A is a perspective view of an exemplary extension device 300 according to one embodiment of the present disclosure, illustrating a front aspect of the exemplary extension device 300. FIG. 10B is a cross-sectional view of the exemplary extension device 300 shown in FIG. 10A. The extension device 300 is substantially similar to the extension device 250 except for the differences described herein. In particular, the extension device 300 includes a plurality of tensioning features 305 located along a channel 310, which extends through a body 315 from a first end aperture 320 to a second end aperture 322. The body 315 includes an outer aperture 324 is formed as a wide slot-like opening defined by a first edge 326 and a second edge 328. The tensioning features 305 are substantially similar in shape and size to the tensioning features 290 described above. In the exemplary embodiment shown in FIGS. 10A and 10B, the tensioning features 305 are located in a central portion 330 of the body 315 and comprise slots or cutouts in the second edge 328. Terminal portions 332a, 332b and the upper edge 326 of the extension device 300 lack the tensioning features 305. The tensioning features 305 extend through the body 315 from an outer surface 334 to an inner surface 336 of the extension device 300.

In the pictured embodiment of FIG. 10A, the extension device 300 is in an unconstrained condition, and the tensioning features 305 comprise teardrop-shaped slots (i.e., when the extension device is in a generally native or relaxed condition). The tensioning features 305 are shaped and arranged on an outer side 338 of the body 315 to facilitate the grasping of ocular tissue (i.e., the iris 130 and/or the scleral spur 203). In FIG. 10A, the tensioning features 305 are spaced symmetrically along the central portion 330 of the extension device 300. In other embodiments, the tensioning features 305 may be arranged asymmetrically. Like the extension device 250 described above, the extension device 300 is shaped and configured to be implanted within the irideocorneal angle 204. Unlike the extension device 250, because the tensioning features 305 are positioned on only the second or lower edge 328 of the body 315, the extension device 300 is shaped and configured to grasp the iris 130 (and/or the scleral spur 203) instead of the trabecular meshwork 150. As best shown in FIG. 10B, the second edge 328 of the extension device 300 is positioned lower on the extension device 300 (in comparison with the second edge 275 of the extension device 250). Because the tensioning features 305 are disposed upon the second or lower edge 328 of the body 315, and because the second edge is disposed upon a lower side of the extension device 300, the tensioning features 305 are positioned to engage with the tissue underlying the extension device 300 (e.g., the iris 130, the scleral spur 203, and/or the ciliary muscle 140) to extend or stretch the trabecular meshwork 150 and associated downstream ocular structures radially inward toward the center of the iris 130.

Figure 11A:
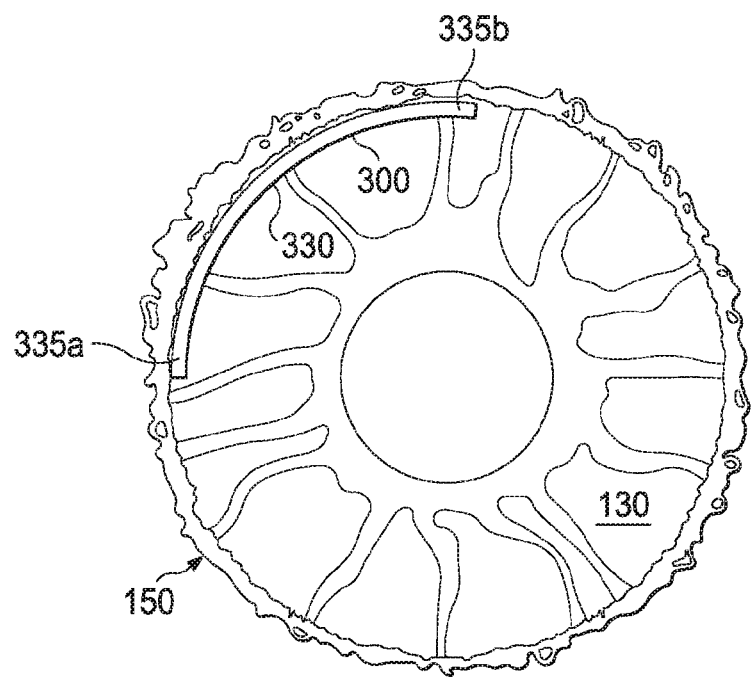
FIGS. 11A and 11B are diagrammatic illustrations of a portion of the exemplary extension device shown in FIG. 10A positioned within an eye according to principles of the present disclosure.
Figure 11B:
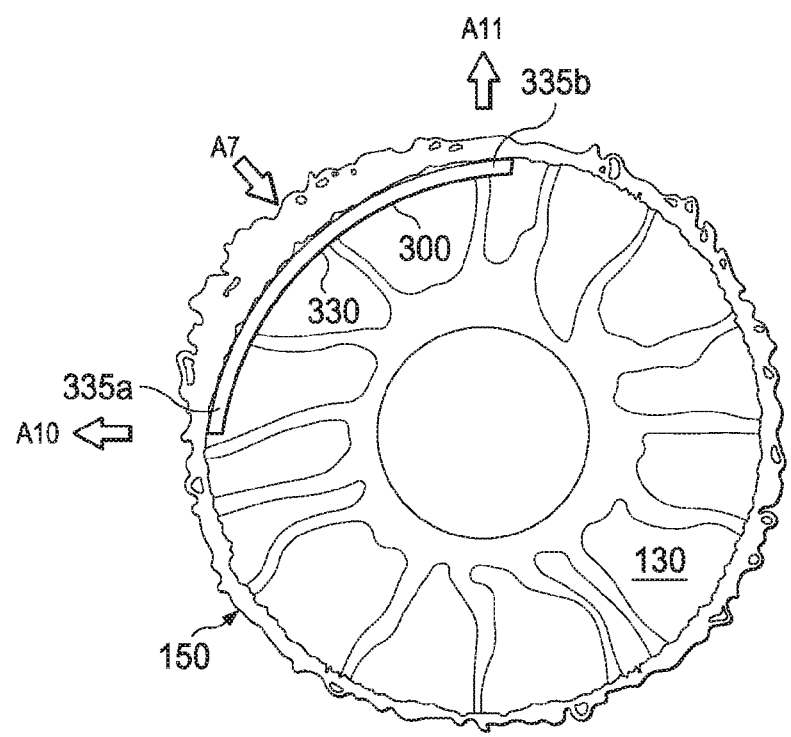

FIGS. 11A and 11B are diagrammatic illustrations of a portion of the extension device 300 positioned within the eye 10 according to principles of the present disclosure. FIG. 11A illustrates the extension device 300 in a flexed, constrained condition, and FIG. 11B illustrates the exemplary extension device in a relaxed, unconstrained condition. In operation, the implanted extension device 300 acts on the trabecular meshwork 150 in the same fashion as described in FIGS. 9A and 9B with reference to the extension device 250. In particular, the extension device 300 is flexed to a smaller radius of curvature during positioning in the irideocorneal angle 204, hooked onto the underlying ocular tissue (i.e., grasping and retaining the iris 130 and/or the scleral spur 203), and then unflexed to assume a larger radius of curvature. After the extension device 300 grasps the ocular tissue (i.e., the iris 130) and is allowed to unflex, the trabecular meshwork 150 is pulled radially inward in the direction of arrow A7 by the central portion 330 of the body 315 containing the tensioning features 305, and the two terminal portions 334A, 334B of the body 315 compress the trabecular meshwork 150 radially outward in the directions of arrows A10, A11, respectively. Thus, the tensioning features 305 at the central portion 330 of the body 315 allow the extension device 300 to self-retain in the eye 10, while tugging the trabecular meshwork 150 radially inward toward the center of the iris 130, and the terminal portions 334A, 334B (i.e., the tips of the extension device 300) push radially outward into the trabecular meshwork 150 to balance the force and stabilize the device 300. Some implementations of the extension device 300 include additional tensioning features that allow the extension device 300 to self-retain in the eye 10.

Figure 12B:
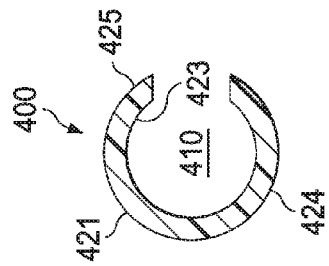
FIG. 12B is a cross-sectional view of the exemplary extension device shown in FIG. 12A.
Figure 12C:
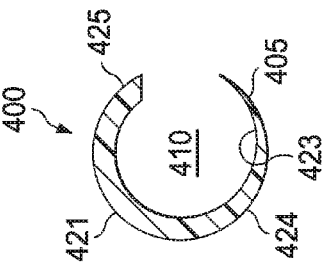
FIG. 12C is a cross-sectional view of the exemplary extension device shown in FIG. 12A.
Figure 12A:
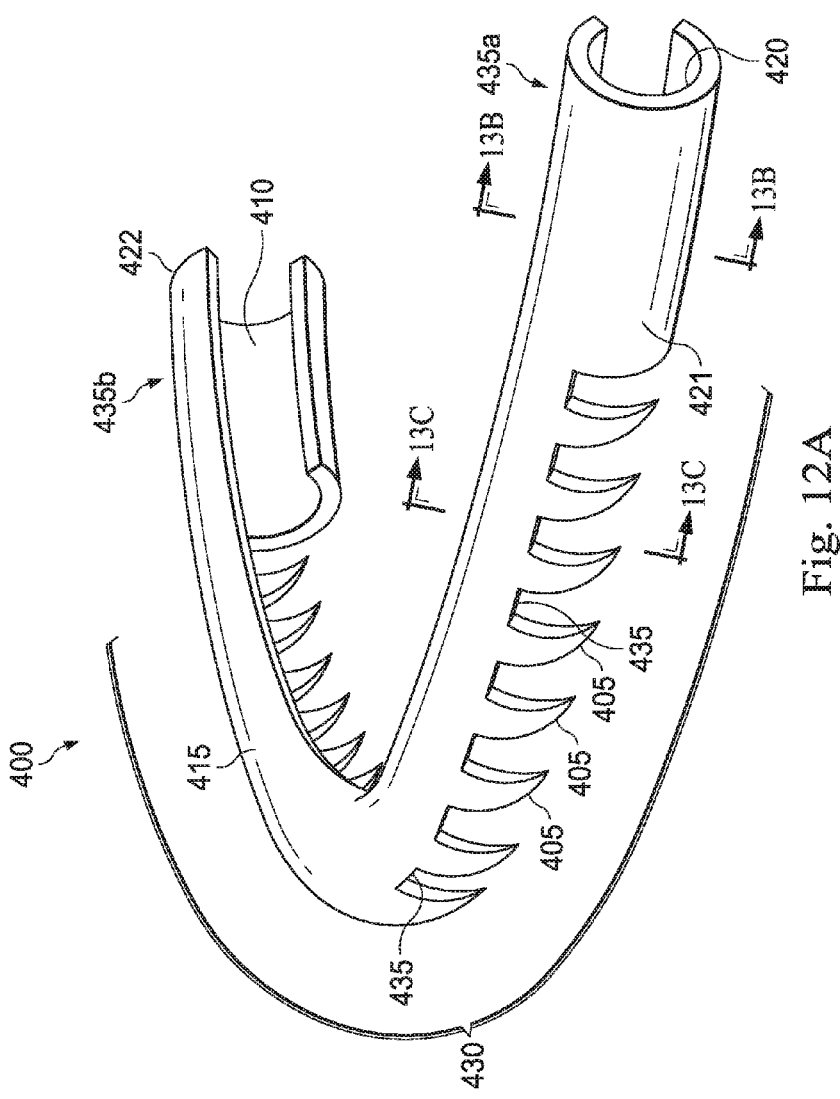
FIG. 12A is a perspective view of an exemplary extension device according to one embodiment of the present disclosure, illustrating a front aspect of the exemplary extension device.

FIG. 12A is a perspective view of an exemplary extension device 400 according to one embodiment of the present disclosure, illustrating a front aspect of the extension device 400. FIG. 12B is a cross-sectional view of the extension device 400 shown in FIG. 12A through the line 12B-12B. FIG. 12C is a cross-sectional view of the extension device 400 shown in FIG. 12A through the line 12C-12C. The extension device 400 is substantially similar to the extension device 250 except for the differences described herein. In particular, the extension device 400 includes a plurality of tensioning features 405 located along a channel 410, which has a cylindrical volume and extends through a body 415 from a first end aperture 420 to a second end aperture 422. The channel 410 is defined by an inner side 425 of the body 415. The tensioning features 405 are substantially similar in purpose to the tensioning features 290 described above except for the shape, size, and functionality differences described herein. In the pictured embodiment, the tensioning features 405 are positioned on an outer side 421 of the body 415 (as in the extension device 250 described above). The tensioning features 405 are shaped as hooks or arcuate prongs that form a central portion 430 of the extension device 400 on an outer surface 424 of the body 415, and converging toward an inner surface 423. The tensioning features 405 are shaped and arranged upon the body 415 to facilitate the grasping of ocular tissue (i.e., the trabecular meshwork 150, the iris 130, and/or the scleral spur 203). In FIG. 12A, the tensioning features 405 are spaced symmetrically along a first edge 435 of the central portion 430 of the extension device 400. In other embodiments, the tensioning features 405 may be arranged asymmetrically. In the pictured embodiment, the tensioning features 405 are shaped like hook-like protrusions that angle inward toward an inner side 425 of the body 415. As shown in FIG. 12C, the tensioning features 405 may terminate in a sharp or angular point to facilitate easier insertion into the ocular tissue. In other embodiments, the tensioning features 405 may have any of a variety of shapes that are capable of grasping ocular tissue, including, without limitation, angular protrusions, barb-like protrusions, finger-like protrusions, etc. In some embodiments, the tensioning features 405 may be cut from a Nitinol tube (e.g., the body 415 may be a Nitinol tube).

Figure 13A:
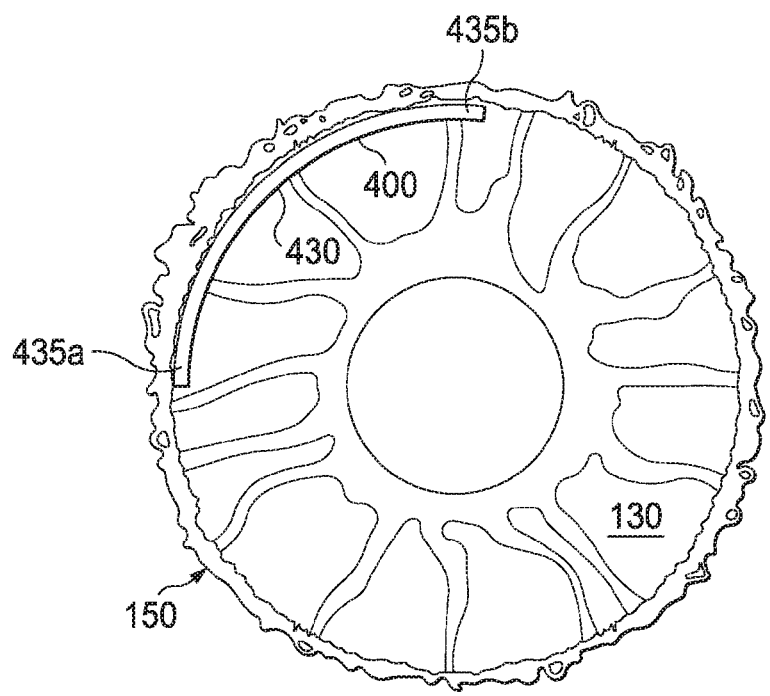
FIGS. 13A and 13B are diagrammatic illustrations of a portion of the exemplary extension device shown in FIG. 12A positioned within an eye according to principles of the present disclosure.
Figure 13B:
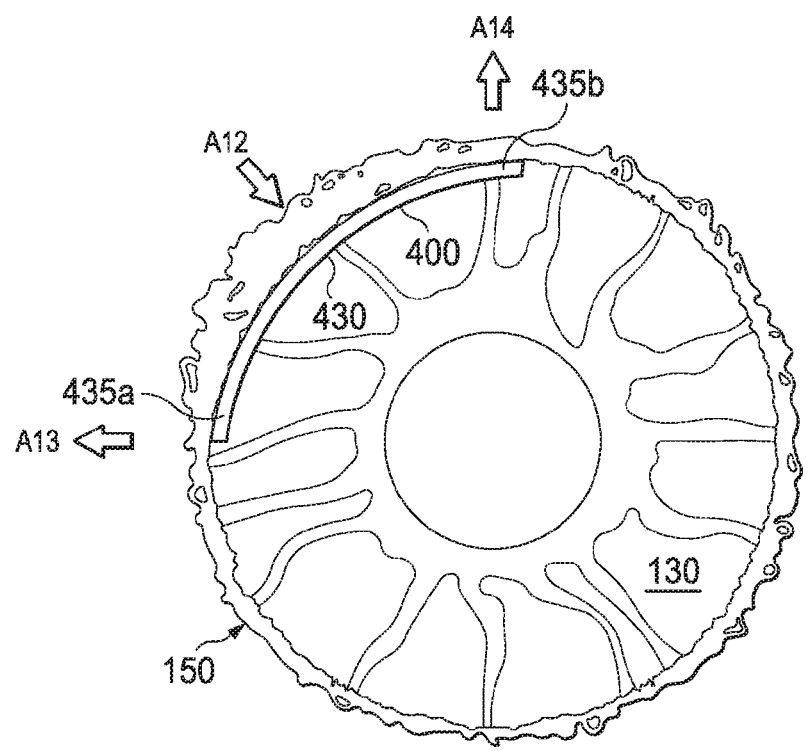

FIGS. 13A and 13B diagrammatic illustrations of a portion of the extension device positioned within the eye 10 according to principles of the present disclosure. FIG. 13A illustrates the extension device 400 in a flexed, constrained condition, and FIG. 13B illustrates the exemplary extension device in a relaxed, unconstrained condition. Unlike the extension device 250, because the tensioning features 405 are shaped to hook into ocular tissue from the inner side 425 instead of the outer side 421 of the body 415, the extension device 400 is shaped and configured to more easily grasp the iris 130 (and/or the scleral spur 203) than the trabecular meshwork 150. In operation, the implanted extension device 400 acts on the trabecular meshwork 150 in a similar manner as described in FIGS. 9A and 9B with reference to the extension device 250. In particular, the extension device 400 is flexed to a smaller radius of curvature during positioning in the irideocorneal angle 204, hooked onto the ocular tissue (i.e., the iris 130, the scleral spur 203, and/or the trabecular meshwork 150), and then unflexed to assume a larger radius of curvature. After the extension device grasps the ocular tissue and is unflexed, the trabecular meshwork 150 is pulled radially inward in the direction of arrow A12 by the central portion 430 of the body 415 containing the tensioning features 405, and two terminal portions 435a, 435b of the body 415 compress the trabecular meshwork 150 radially outward in the directions of arrows A13, A14, respectively. Thus, the tensioning features 405 at the central portion 430 of the body 415 allow the extension device 400 to self-retain in the eye 10, while tugging the trabecular meshwork 150 radially inward toward the center of the iris 130, and the terminal portions 435a, 435b (i.e., the tips of the extension device 400) push radially outward into the trabecular meshwork 150 to balance the force and stabilize the device 400.

Figure 14:
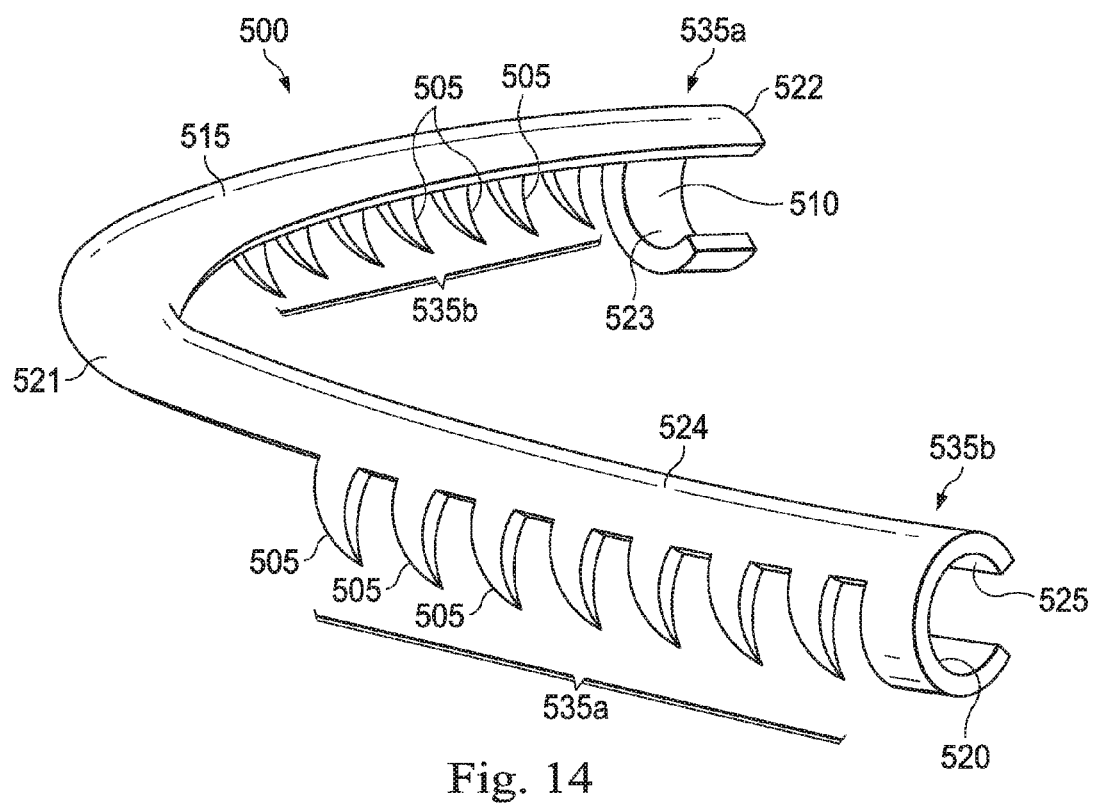
FIG. 14 is a perspective view of an exemplary extension device according to one embodiment of the present disclosure, illustrating a front aspect of the exemplary extension device.

FIG. 14 is a perspective view of an exemplary extension device 500 according to one embodiment of the present disclosure, illustrating a front aspect of the exemplary extension device. The extension device 500 is substantially similar to the extension device 400 except for the differences described herein. In particular, the extension device 500 includes a plurality of tensioning features 505 located along a channel 510, which extends through a body 515 from a first end aperture 520 to a second end aperture 522. The tensioning features 505 are substantially similar in shape and size to the tensioning features 405 described above except for the positional differences described herein. In the pictured embodiment, the tensioning features 505 are positioned on an outer side 521 of the body 515 (as in the extension device 400 described above), and the tensioning features 505 extend through the body 515 from an inner surface 523 to an outer surface 524. However, instead of being positioned in a central portion 530 of the body 515 (as in the extension device 400 described above), the tensioning features 505 are positioned in two terminal portions 535a, 535b of the body 515. The tensioning features 505 are shaped and arranged within the body 515 to facilitate the grasping of ocular tissue (i.e., the trabecular meshwork 150, the iris 130, and/or the scleral spur 203). In FIG. 14, the tensioning features 505 are spaced symmetrically along the terminal portions 535a, 535b of the extension device 500. In other embodiments, the tensioning features 505 may be arranged asymmetrically.

Figure 15A:
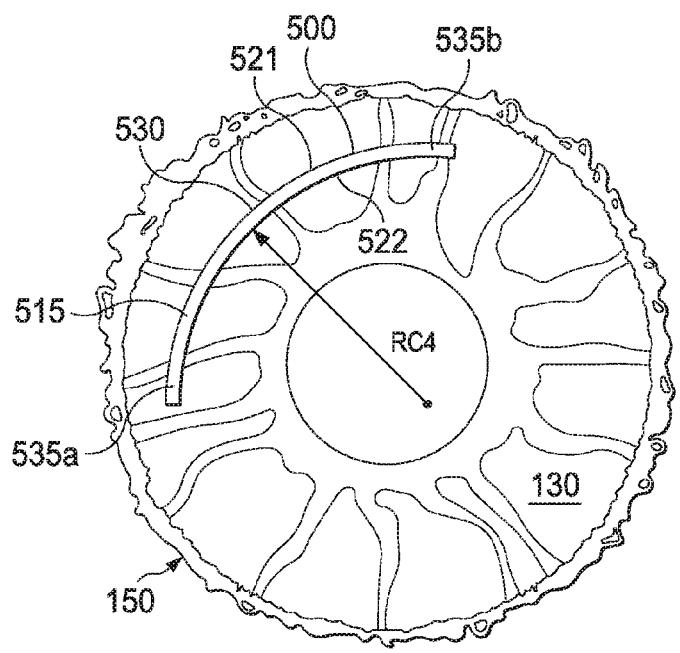
FIGS. 15A and 15B are diagrammatic illustrations of a portion of the exemplary extension device shown in FIG. 144A positioned within an eye according to principles of the present disclosure.
Figure 15B:
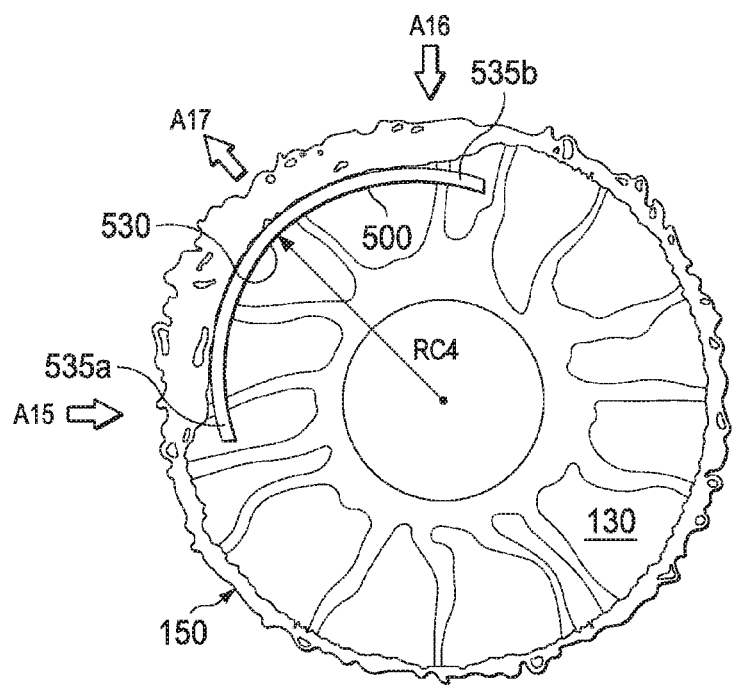

FIGS. 15A and 15B diagrammatic illustrations of a portion of the extension device 500 positioned within the eye 10 according to principles of the present disclosure. FIG. 15A illustrates the extension device 500 in a flexed, constrained condition, and FIG. 15B illustrates the exemplary extension device in a relaxed, unconstrained condition. Like the extension device 400, because the tensioning features 505 are shaped to hook into ocular tissue from the inner side 525 instead of the outer side 521 of the body 515, the extension device 500 is shaped and configured to more easily grasp the iris 130 (and/or the scleral spur 203) than the trabecular meshwork 150. In operation, the implanted extension device 500 acts on the trabecular meshwork 150 in a reverse flex manner than described with reference to the extension device 400 in FIGS. 13A and 13B. In particular, the extension device 500 is flexed to a larger radius of curvature RC4 (i.e., larger than the radius of curvature of the irideocorneal angle) during positioning in the irideocorneal angle 204, hooked onto the ocular tissue (i.e., the iris 130, the scleral spur 203, and/or the trabecular meshwork 150), and then unflexed to assume a smaller radius of curvature RC5. After the extension device 500 grasps the ocular tissue and is unflexed, the trabecular meshwork 150 is pulled radially inward in the directions of arrows A15, A16, respectively by the terminal portions 535a, 535b of the body 515 containing the tensioning features 505, and the central portion 530 of the body 515 compresses the trabecular meshwork 150 radially outward in the direction of arrow A17. Thus, the tensioning features 505 allow the extension device 500 to self-retain in the eye 10, while tugging two separate areas of the iris 130 and, consequently, the trabecular meshwork 150 radially inward toward the center of the iris 130, and the central portion 530 of the extension device 500 pushes radially outward into the trabecular meshwork 150 to balance the force and stabilize the device 500.

FIGS. 16A-16D illustrate an exemplary method of implanting the extension device 250 shown in FIG. 6A into the eye 10 using an exemplary delivery device 600 according to the principles of the present disclosure. Although insertion of the extension device 250 is shown, a similar implantation method may be employed for the other embodiments described herein except for the reverse flex method of implantation mentioned above with respect to FIG. 15B.

Figure 16A:
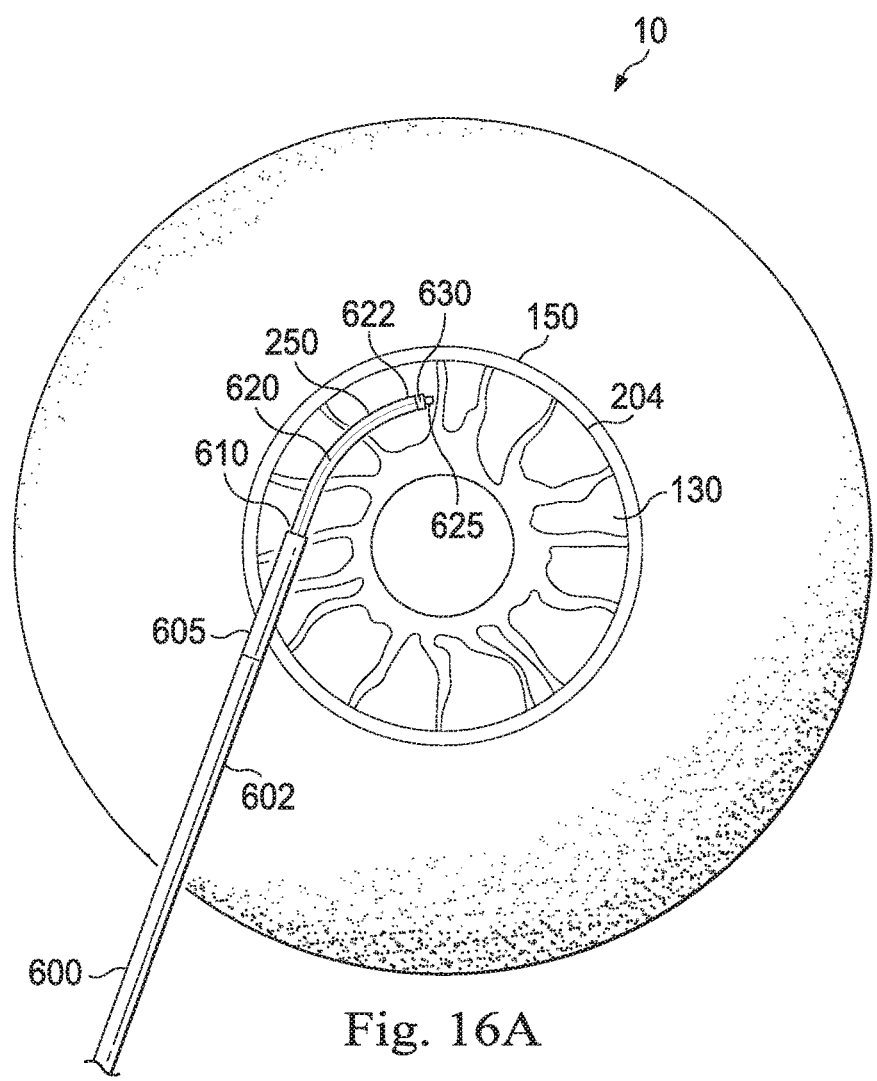
FIGS. 16A-16D illustrate top plan views of the exemplary extension device shown in FIG. 6A being inserted into an eye according to the principles of the present disclosure.

FIG. 16A illustrates a diagrammatic view of an exemplary delivery device 600 according to one embodiment of the present disclosure. The delivery device 600 is a cylindrical tube 602 through which the extension device 250 may be placed at a desired location in the eye 10 (and may be removed from the eye 10) as desired by the surgeon in a controlled way. The delivery device 600 includes a distal portion 605 that may be articulable so the distal portion 605 may be precisely curved into a desired location within the eye 10. In some embodiments, the distal portion 605 may be steerable, articulating, or shapeable in a manner that facilitates the proper approach of the extension device 250 toward the desired ocular tissues. In some instances, aspects of the delivery device 600 include features disclosed in U.S. Patent Application No. 2013/0035551, entitled "Articulating Ophthalmic Surgical Probe," filed on Aug. 1, 2012, and U.S. Patent Application No. 2015/0223976, entitled "Manufacturing an Articulating Ophthalmic Surgical Probe," filed on Feb. 3, 2015, which are incorporated herein by reference in its entirety. The delivery device 600 includes a deployment mechanism (not shown) that ejects the extension device 250 from a first lumen (not shown) of the delivery device 600 into the eye 10. The delivery device 600 may also include a second lumen (not shown) through which irrigation, drugs, or other medicaments and/or suction may be applied to the implant site.

In the method of placing the extension device 250 shown in FIGS. 16A-16D, the delivery device 600 is used to place the extension device 250 at the appropriate location adjacent the trabecular meshwork 150 in the irideocorneal angle 204 of the eye 10. Prior to placing the extension device 250 within the eye 10, the surgeon may fill the anterior chamber 170 in a conventional manner (through, for example, a small incision (not shown) in the cornea 120) with a viscoelastic fluid to prevent the cornea 120 from collapsing and to provide lubrication and support for the subsequent insertion of surgical instruments. In some instances, the delivery device 600 is placed through a cannula (not shown) that has been pre-positioned through the cornea. As shown in FIG. 16A, the surgeon may insert the delivery device 600 into the anterior chamber 170 and guide the distal portion 605 near or into contact with the trabecular meshwork 150 within the irideocorneal angle 204. In some embodiments of the delivery device 600, a distal end 610 is sharpened. In such embodiments, the surgeon may not need a cannula. For example, the surgeon may push the distal end 610 through the cornea 120 so that the delivery device 600 tunnels through the cornea 120 directly into the anterior chamber 170. After the distal portion 605 is properly positioned relative to the trabecular meshwork 150, the surgeon may articulate the distal portion 605 to facilitate delivery of the extension device 250 into the irideocorneal angle 204 at the appropriate angle (e.g., a tangential approach to the irideocorneal angle 204 and/or the trabecular meshwork 150). The appropriate angle may be selected to minimize trauma to the ocular tissues from unnecessary maneuvering, shaping, or repositioning of the extension device 250 within the anterior chamber 170. The delivery device 600 includes a push mechanism (e.g., a plunger element, not shown) longitudinally disposed within a tubular housing for selectively applying distally directed force to a proximal end of the extension device 250. In some embodiments, the delivery instrument 600 includes an actuating mechanism configured to cause longitudinal translation of the push mechanism along a longitudinal axis of the housing to displace the extension device from a lumen of the delivery device 600 into the anterior chamber 170. After the distal end 610 of the delivery device 600 is desirably positioned within the anterior chamber 170, the extension device 250 may be advanced into the anterior chamber 170 through the delivery device 600 and positioned in the irideocorneal angle 204 in a flexed condition.

Referring to FIG. 16A, the delivery device 600 includes a guiding element 620 that is shaped and sized to extend through the channel 280 of the extension device 250. In some embodiments, the guiding element 620 may be configured to extend alongside the entire length L1 of the extension device 250. The guiding element 620 is movable with the extension device 250 within the delivery device 600. When the guiding element 620 is coupled to the extension device 250, the guiding element 620 moves in concert with the extension device 250 through the delivery device 600. When the guiding element 620 is detached from the extension device 250, the guiding element 620 may move independently of the extension device 250.

Figure 16B:
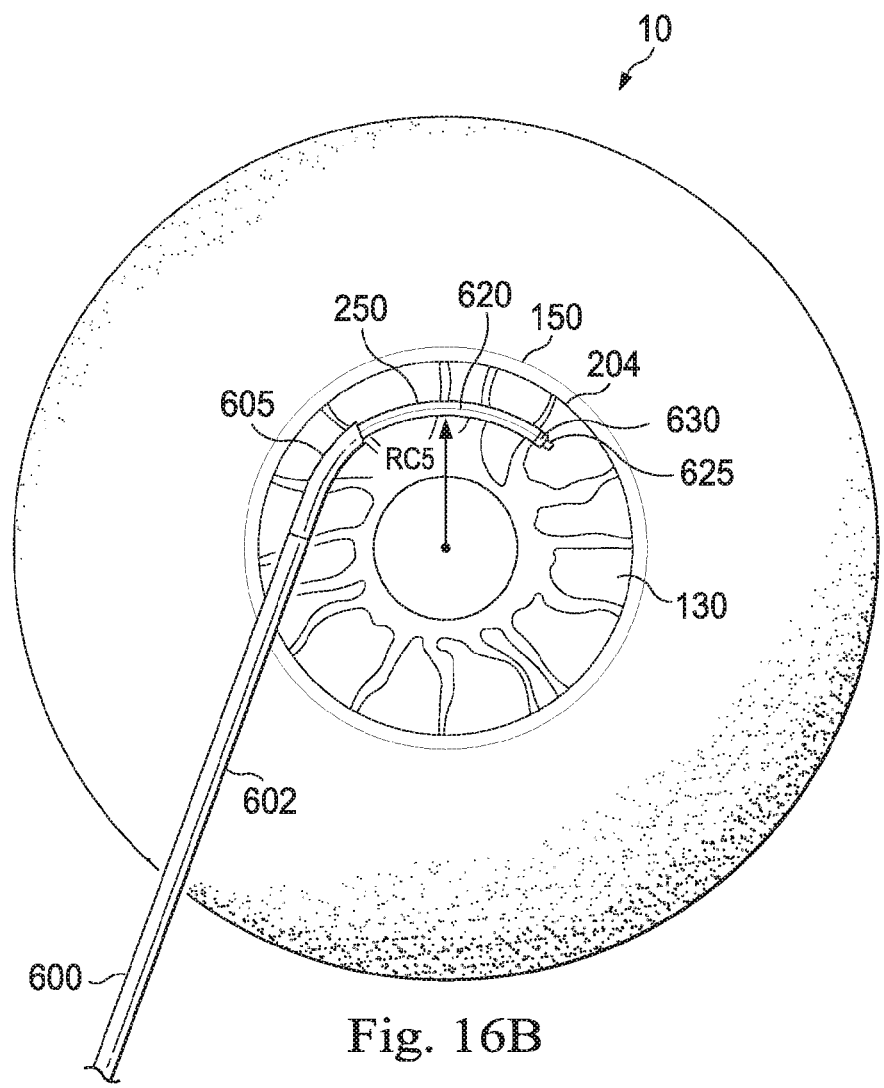

When the extension device 240 is passed into and through a lumen of the delivery device 600, the extension device 240 is in a constrained, straightened condition. As the extension device 250 is advanced out of the delivery device 600 and into the anterior chamber 170, the guiding element 620 maintains the extension device 250 in a desired curvature during implantation of the extension device 250 into the irideocorneal angle 204. For example, as shown in FIG. 16B, the guiding element 620 may be curved to forcibly constrain or flex the extension device 250 to assume a radius of curvature RC5 that is smaller than the radius of curvature of the extension device 250 in an unflexed state. Another function of the guiding element 620 may be to block the apertures of the extension device 250 and minimize interference between the device and the ocular tissue as the extension device 250 is advanced into the irideocorneal angle 204.

In the pictured embodiment, the guiding element 620 comprises a pull wire that extends through the extension device 250 and removably couples to a leading end 622 (e.g., the end aperture 260b) of the extension device 250. In some embodiments, the guiding element 620 simply grasps or hooks onto the end aperture 260b of the extension device 250. In other embodiments, the guiding element 620 may include an instrument engaging feature 625 that is shaped and configured to detachably couple with the extension device 250. In some embodiments, the leading end 622 of the extension device 250 may include an attachment feature 630 that is shaped and configured to matingly engage with the instrument engagement feature 625 of the guiding element 620. In various embodiments, the instrument engaging feature 625 may include any of a variety of connecting features, including, by way of non-limiting example, screw-like external threads, internal threads, grooves, protrusions, loops, and/or hooks. For example, in one embodiment, the instrument engaging feature 625 of the guiding element 620 may comprise external threads configured to detachably engage with internal threads forming the attachment feature 630 of the extension device 250. Thus, in one example, before insertion of the extension device 250, the instrument engaging feature 625 of the guiding element 620 could be screwed into the attachment feature 630 of the leading end 622 of the extension device 250.

Figure 16C:
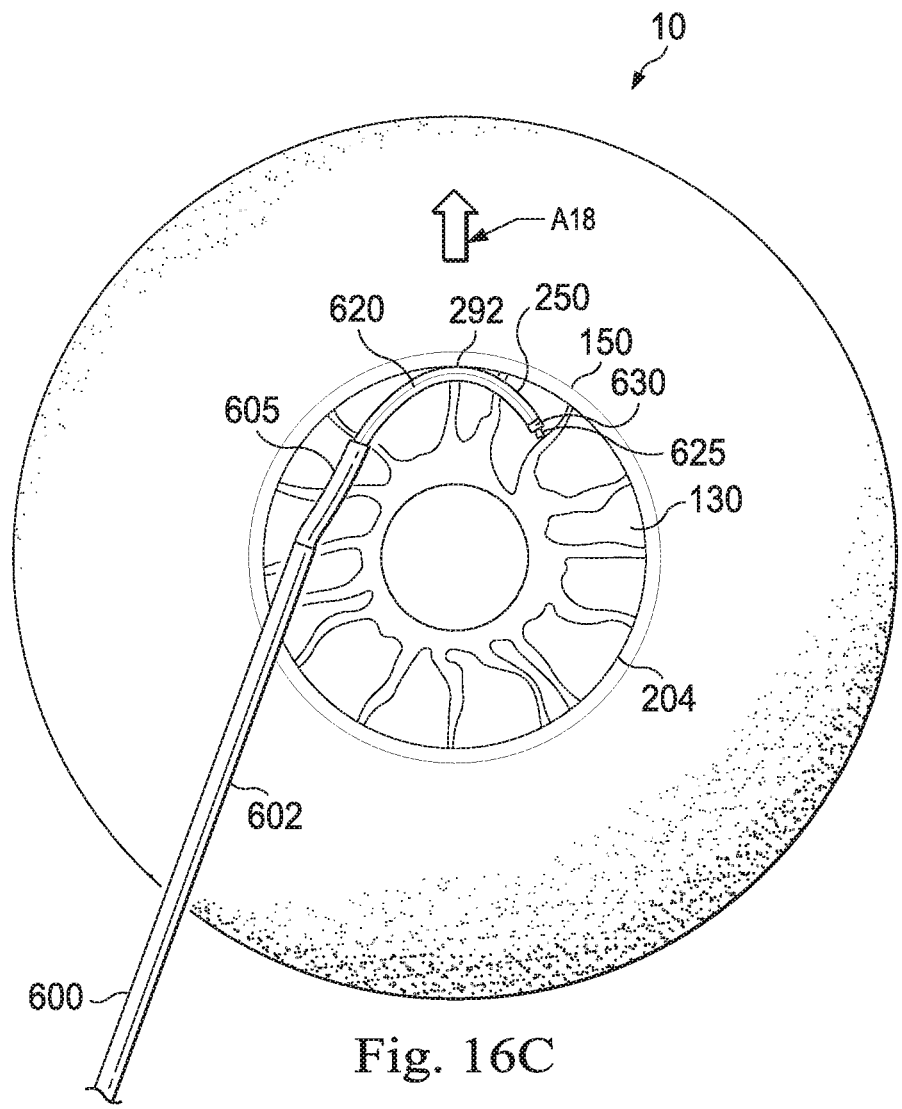
Figure 16D:
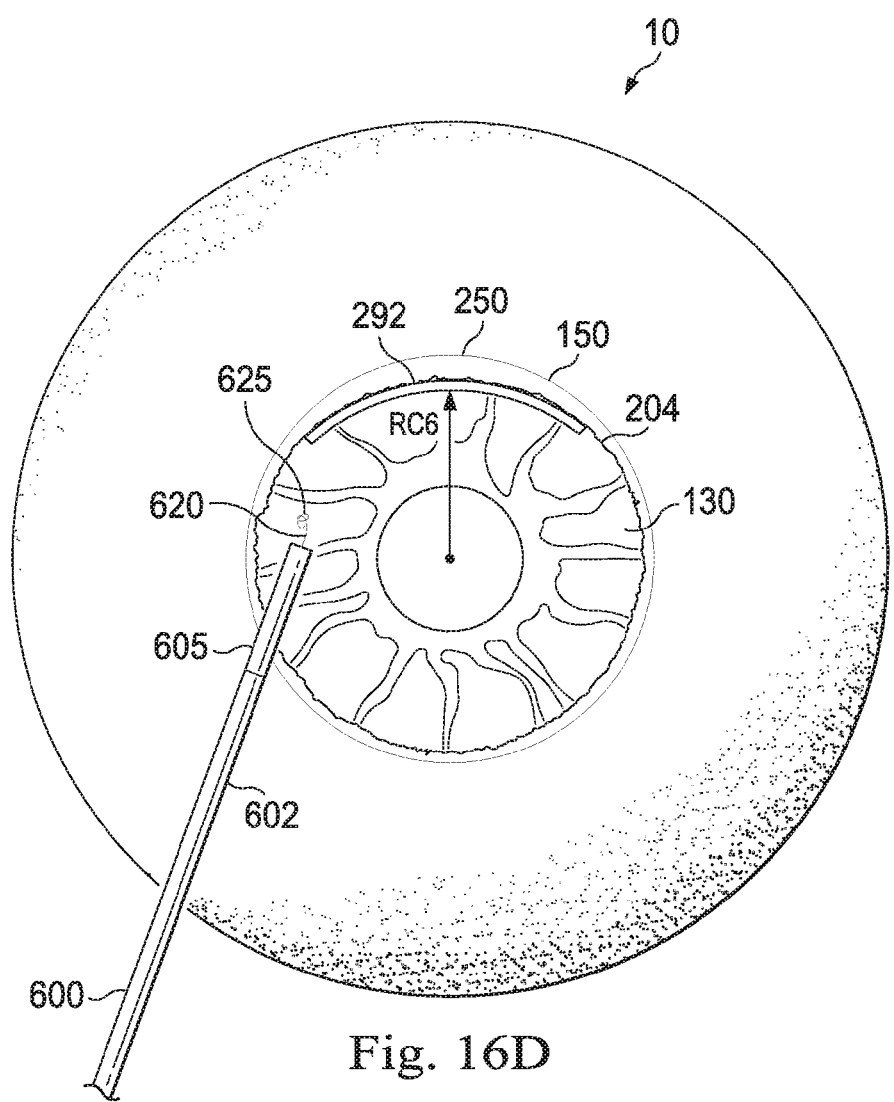

During implantation of the extension device 250, as shown in FIG. 16C, the surgeon may employ the guiding element 620 to push the central portion 292 of the extension device (i.e., the portion with the tensioning features 290) radially outward in the direction of arrow A18 into the trabecular meshwork 150. After adequate amounts of ocular tissue have been surrounded by the tensioning features 290 of the extension device 250, the guiding element 620 may be withdrawn, as shown in FIG. 16D, to allow the extension device 250 to unflex and assume a larger radius of curvature RC6. In one example, the instrument engaging feature 625 of the guiding element 620 can be unscrewed from the attachment feature 630 of the leading end 622 of the extension device 250, and the guiding element 620 can be proximally withdrawn from within or alongside the extension device 250. When the guiding element 620 is withdrawn from the extension device 250, the extension device 250 is released and unflexes to assume the radius of curvature RC6. Generally, the radius of curvature RC6 is approximately equal to the radius of curvature of the iris 130 and/or the irideocorneal angle 204. As the extension device 250 unflexes and assumes the larger radius of curvature RC6, the trabecular meshwork 150 in the region adjacent the central portion 292 stretches radially inward to increase the surface area of the trabecular meshwork (e.g., as described above with reference to FIG. 9B). Thereafter, the delivery device 600 and the guiding element 620 are removed from the eye 10, leaving the extension device 250 in place in the irideocorneal angle 204 as shown in FIG. 16D.

The various trabecular meshwork extension devices and systems described herein are shaped and configured to expand the trabecular meshwork upon implantation and to increase the surface area of the trabecular meshwork (and possibly other ocular structures downstream of the trabecular meshwork such as collector channels and Schlemm's canal), thereby facilitating drainage of aqueous humor from the eye. The extension devices described herein can assume an unexpanded condition to facilitate atraumatic insertion into and removal from an eye through a primary incision, can assume a flexed condition to aid in proper positioning against the relevant ocular tissues, and can unflex to assume a predetermined, expanded condition within the eye after implantation. Moreover, the various extension device embodiments described herein can stabilize and self-retain their position within an eye.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

I claim:

1. An extension device to extend trabecular meshwork within an irideocorneal angle of an eye of a patient, the device comprising:
  a flexible body having a curved longitudinal axis, a channel extending from a first end to a second end, an inner convex side, and an outer concave side, the body being flexible between a first flexed condition and a second unflexed condition, the body being sized and configured to be disposed adjacent to the trabecular meshwork and within the irideocorneal angle; and
  a plurality of tensioning features disposed on the body, each tensioning feature shaped and sized to grasp the trabecular meshwork within the irideocorneal angle and to pull the trabecular meshwork in a direction away from a Schlemm's canal of an eye so as to expand the Schlemm's canal when the flexible body is in the flexed condition,
  wherein the body has a first radius of curvature in the first flexed condition and a second radius of curvature in the unflexed condition, each of the plurality of tensioning features comprises a slot-like opening, each slot-like opening assumes an open condition when the body assumes the first flexed condition in which two sides of each of the slot-like opening do not touch each other, and a closed condition when the body assumes the second unflexed condition in which the two sides of each of the slot-like openings touch each other.

2. The extender device of claim 1, wherein the first radius of curvature is smaller than the second radius of curvature.

3. The extender device of claim 1, wherein the second radius of curvature is smaller than the first radius of curvature.

4. The extender device of claim 1, wherein the body has a curved, cylindrical, elongate shape.

5. The extender device of claim 1, wherein the body has an annular, open, generally circular shape.

6. The extender device of claim 1, wherein each of the plurality of tensioning features comprises a hook extending from an inner surface to an outer surface of the body, the hook configured to pierce and retain ocular tissue.

7. The extender device of claim 1, wherein the plurality of tensioning features are positioned on a central portion of the body.

8. The extender device of claim 1, wherein the plurality of tensioning features are positioned on peripheral portions of the body.

9. The extender device of claim 1, wherein the plurality of tensioning features are positioned on the inner, concave side of the body.

10. The extender device of claim 1, wherein the plurality of tensioning features are positioned on the outer, convex side of the body.

11. The extender device of claim 1, wherein the plurality of tensioning features are uniform in shape and size.

12. The extender device of claim 1, wherein the plurality of tensioning features are symmetrically arranged on the body.

13. A system to extend trabeuclar meshwork within an irideocorneal angle of an anterior chamber of an eye of a patient, comprising:
  flexible body having a curved longitudinal axis, a channel extending from a first end to a second end, an inner convex side, and an outer concave side, the body being flexible between a first radius of curvature in a first flexed condition and a second radius of curvature in a second unflexed condition, the body being sized and configured to be disposed adjacent to the trabecular meshwork and within the irideocorneal angle;
  a plurality of tensioning features disposed on the body, each tensioning feature being shaped and sized to grasp the trabecular meshwork within the irideocorneal angle and to pull the trabecular meshwork in a direction away from a Schlemm's canal of an eye so as to expand the Schlemm's canal when the flexible body is in the flexed condition;
  wherein the body has a first radius of curvature in the first flexed condition and a second radius of curvature in the unflexed condition, each of the plurality of tensioning features comprises a slot-like opening, each slot-like opening assumes an open condition when the body assumes the first flexed condition in which two sides of each of the slot-like opening do not touch each other, and a closed condition when the body assumes the second unflexed condition in which the two sides of each of the slot-like openings touch each other; and a delivery device including a push mechanism configured to advance the flexible body and a guiding element into the anterior chamber, the guiding element removably coupled to the body and configured to constrain the curvature of the body when coupled to the body.

14. The system of claim 13, wherein the first radius of curvature is smaller than the second radius of curvature.

15. The system of claim 13, wherein the second radius of curvature is smaller than the first radius of curvature.

16. The system of claim 13, wherein each of the plurality of tensioning features comprises a hook extending from an inner surface to an outer surface of the body, the hook configured to pierce and retain ocular tissue.

17. The system of claim 13, wherein the plurality of tensioning features are positioned on a central portion of the body.

18. The system of claim 13, wherein the plurality of tensioning features are positioned on peripheral portions of the body.

19. The system of claim 13, wherein the plurality of tensioning features are positioned on the inner, concave side of the body.

20. The system of claim 13, wherein the plurality of tensioning features are positioned on the outer, convex side of the body.

\* \* \* \* \*